US008500774B2

United States Patent
McGuckin, Jr. et al.

(10) Patent No.: US 8,500,774 B2
(45) Date of Patent: Aug. 6, 2013

(54) VEIN FILTER

(75) Inventors: James F. McGuckin, Jr., Radnor, PA (US); James E. Bressler, Langhorne, PA (US); David M. Schaller, Wallingford, PA (US)

(73) Assignee: Rex Medical, L.P., Conshohocken, PA (US)

( * ) Notice: Subject to any disclaimer, the term of this patent is extended or adjusted under 35 U.S.C. 154(b) by 602 days.

(21) Appl. No.: 12/551,605

(22) Filed: Sep. 1, 2009

(65) Prior Publication Data

US 2010/0049239 A1 Feb. 25, 2010

Related U.S. Application Data

(63) Continuation-in-part of application No. 11/888,929, filed on Aug. 3, 2007, now Pat. No. 8,062,326, and a continuation-in-part of application No. 10/889,429, filed on Jul. 12, 2004, now Pat. No. 7,704,266, and a continuation-in-part of application No. 10/805,796, filed on Mar. 22, 2004, now Pat. No. 7,338,512.

(60) Provisional application No. 61/191,903, filed on Sep. 12, 2008, provisional application No. 60/840,888, filed on Aug. 29, 2006, provisional application No. 60/572,274, filed on May 18, 2004, provisional application No. 60/538,379, filed on Jan. 22, 2004.

(51) Int. Cl.
*A61F 2/01* (2006.01)

(52) U.S. Cl.
USPC .......................................... 606/200

(58) Field of Classification Search
USPC ................ 606/108, 191, 194, 200; 623/23.72
See application file for complete search history.

(56) References Cited

U.S. PATENT DOCUMENTS

| 3,744,492 A | 7/1973 | Leibinsohn |
| 3,952,747 A | 4/1976 | Kimmel, Jr. |
| 4,266,815 A | 5/1981 | Cross |
| 4,425,908 A | 1/1984 | Simon |
| 4,494,531 A | 1/1985 | Gianturco |

(Continued)

FOREIGN PATENT DOCUMENTS

| DE | 3429850 | 2/1986 |
| WO | WO 9312723 | 7/1993 |

(Continued)

OTHER PUBLICATIONS

B. Braun Medical, Inc. Vena Tech™ Vena Cava Filters, Feb. 2000.

(Continued)

*Primary Examiner* — Kathleen Holwerda
(74) *Attorney, Agent, or Firm* — Neil D. Gershon

(57) ABSTRACT

A vessel filter comprising a first distal region terminating at a first end and a second proximal region terminating at a second end of the filter and movable between a collapsed position for delivery to the vessel and an expanded position for placement within the vessel. The first region has a filter portion having a converging region to direct particles toward the center of the filter. The second region is flared in the expanded position to have a transverse dimension increasing toward a second end portion opposite the filter portion and includes a vessel engaging portion at the second end portion. The first region has a retrieval hook and a spacer forming a looped region extending radially from the first region.

18 Claims, 19 Drawing Sheets

U.S. PATENT DOCUMENTS

| | | | |
|---|---|---|---|
| 4,512,338 A | 4/1985 | Balko et al. |
| 4,619,246 A | 10/1986 | Molgaard-Nielsen et al. |
| 4,643,184 A | 2/1987 | Mobin-Uddin |
| 4,688,553 A | 8/1987 | Metals |
| 4,727,873 A | 3/1988 | Mobin-Uddin |
| 4,781,177 A | 11/1988 | Lebigot |
| 4,793,348 A | 12/1988 | Palmaz |
| 4,817,600 A | 4/1989 | Herms et al. |
| 4,832,055 A | 5/1989 | Palestrant |
| 4,957,501 A | 9/1990 | Lahille et al. |
| 4,990,156 A | 2/1991 | Lefebvre |
| 4,994,069 A | 2/1991 | Ritchart et al. |
| 5,059,205 A | 10/1991 | El-Nounou et al. |
| 5,133,733 A | 7/1992 | Rasmussen et al. |
| 5,152,777 A | 10/1992 | Goldberg et al. |
| 5,234,458 A | 8/1993 | Metals |
| 5,300,086 A | 4/1994 | Gory et al. |
| 5,324,304 A | 6/1994 | Rasmussen |
| 5,344,427 A | 9/1994 | Cottenceau et al. |
| 5,350,398 A | 9/1994 | Pavcnik et al. |
| 5,370,657 A | 12/1994 | Irie |
| 5,375,612 A | 12/1994 | Cottenceau et al. |
| 5,382,261 A | 1/1995 | Palmaz |
| 5,383,887 A | 1/1995 | Nadal |
| 5,405,377 A | 4/1995 | Cragg |
| 5,531,788 A | 7/1996 | Dibie et al. |
| 5,591,197 A | 1/1997 | Orth et al. |
| 5,601,595 A | 2/1997 | Smith |
| 5,626,605 A | 5/1997 | Irie et al. |
| 5,634,942 A | 6/1997 | Chevillon et al. |
| 5,681,347 A | 10/1997 | Catheart et al. |
| 5,683,411 A | 11/1997 | Kavteladze et al. |
| 5,690,671 A | 11/1997 | McGurk et al. |
| 5,709,704 A | 1/1998 | Nott et al. |
| 5,725,552 A | 3/1998 | Kotula et al. |
| 5,733,294 A | 3/1998 | Forber et al. |
| 5,733,329 A | 3/1998 | Wallace et al. |
| 5,746,767 A | 5/1998 | Smith |
| 5,755,779 A | 5/1998 | Horiguchi |
| 5,755,790 A | 5/1998 | Chevillon et al. |
| 5,776,162 A | 7/1998 | Kleshinski |
| 5,782,748 A | 7/1998 | Palmer et al. |
| 5,795,322 A | 8/1998 | Boudewijn |
| 5,800,457 A | 9/1998 | Gelbfish |
| 5,810,874 A | 9/1998 | Lefebvre |
| 5,836,968 A | 11/1998 | Simon et al. |
| 5,853,420 A | 12/1998 | Chevillon et al. |
| 5,893,869 A | 4/1999 | Barnhart et al. |
| 5,895,398 A | 4/1999 | Wensel et al. |
| 5,895,410 A | 4/1999 | Forber et al. |
| 5,911,717 A | 6/1999 | Jacobsen et al. |
| 5,968,071 A | 10/1999 | Chevillon et al. |
| 5,976,172 A | 11/1999 | Homsma et al. |
| 5,984,947 A | 11/1999 | Smith |
| 6,007,558 A | 12/1999 | Ravenscroft et al. |
| 6,013,093 A | 1/2000 | Nott et al. |
| 6,042,598 A | 3/2000 | Tsugita et al. |
| 6,059,825 A | 5/2000 | Hobbs et al. |
| 6,063,113 A | 5/2000 | Kavteladze et al. |
| 6,066,158 A | 5/2000 | Engelson et al. |
| 6,080,178 A | 6/2000 | Meglin |
| 6,093,196 A | 7/2000 | Okada |
| 6,093,199 A | 7/2000 | Brown et al. |
| 6,096,052 A | 8/2000 | Callister et al. |
| 6,099,549 A | 8/2000 | Bosma et al. |
| 6,117,154 A | 9/2000 | Barbut et al. |
| 6,123,715 A | 9/2000 | Amplatza |
| 6,126,673 A | 10/2000 | Kim et al. |
| 6,146,404 A | 11/2000 | Kim et al. |
| 6,152,946 A | 11/2000 | Broome et al. |
| 6,165,179 A | 12/2000 | Catheart et al. |
| 6,165,198 A | 12/2000 | McGurk et al. |
| 6,168,579 B1 | 1/2001 | Tsugita |
| 6,168,603 B1 | 1/2001 | Leslie et al. |
| 6,171,327 B1 | 1/2001 | Daniel et al. |
| 6,171,328 B1 | 1/2001 | Addis |
| 6,179,851 B1 | 1/2001 | Barbut et al. |
| 6,179,859 B1 | 1/2001 | Bates et al. |
| 6,187,025 B1 | 2/2001 | Machek |
| 6,193,739 B1 | 2/2001 | Chevillon et al. |
| 6,214,025 B1 | 4/2001 | Thistle et al. |
| 6,217,600 B1 | 4/2001 | DiMatteo |
| 6,231,581 B1 | 5/2001 | Shank et al. |
| 6,231,589 B1 | 5/2001 | Wessman et al. |
| 6,235,044 B1 | 5/2001 | Root et al. |
| 6,235,045 B1 | 5/2001 | Barbut et al. |
| 6,241,746 B1 | 6/2001 | Bosma et al. |
| 6,245,012 B1 | 6/2001 | Kleshinski et al. |
| 6,251,122 B1 | 6/2001 | Tsukernik |
| 6,258,026 B1 | 7/2001 | Ravenscroft et al. |
| 6,267,776 B1 | 7/2001 | O'Connell |
| 6,273,901 B1 | 8/2001 | Whitcher et al. |
| 6,280,451 B1 | 8/2001 | Bates et al. |
| 6,280,457 B1 | 8/2001 | Wallace et al. |
| 6,290,721 B1 | 9/2001 | Heath |
| 6,328,755 B1 | 12/2001 | Marshall |
| 6,331,183 B1 | 12/2001 | Suon |
| 6,331,184 B1 | 12/2001 | Abrams |
| 6,342,062 B1 | 1/2002 | Suon et al. |
| 6,342,063 B1 | 1/2002 | DeVries et al. |
| 6,344,041 B1 | 2/2002 | Kupiecki et al. |
| 6,355,051 B1 | 3/2002 | Sisskind et al. |
| 6,368,338 B1 | 4/2002 | Konya et al. |
| 6,383,205 B1 | 5/2002 | Samson et al. |
| 6,402,771 B1 | 6/2002 | Palmer et al. |
| 6,436,120 B1 | 8/2002 | Meglin |
| 6,436,121 B1 | 8/2002 | Blom |
| 6,443,971 B1 | 9/2002 | Boylan et al. |
| 6,443,972 B1 | 9/2002 | Bosma et al. |
| 6,447,530 B1 | 9/2002 | Ostrovsky et al. |
| 6,447,531 B1 | 9/2002 | Amplatz |
| 6,458,139 B1 | 10/2002 | Palmer et al. |
| 6,468,290 B1 | 10/2002 | Weldon et al. |
| 6,482,222 B1 | 11/2002 | Bruckheimer et al. |
| 6,506,205 B2 | 1/2003 | Goldberg et al. |
| 6,517,559 B1 | 2/2003 | O'Connell |
| 6,527,962 B1 | 3/2003 | Nadal |
| 6,537,294 B1 | 3/2003 | Boyle et al. |
| 6,540,767 B1 | 4/2003 | Walak et al. |
| 6,551,342 B1 | 4/2003 | Shen et al. |
| 6,562,058 B2 | 5/2003 | Seguin et al. |
| 6,589,265 B1 | 7/2003 | Palmer et al. |
| 6,599,307 B1 | 7/2003 | Huter et al. |
| 6,605,102 B1 | 8/2003 | Mazzocchi et al. |
| 6,652,558 B2 | 11/2003 | Patel et al. |
| 6,656,202 B2 | 12/2003 | Papp et al. |
| 6,660,021 B1 | 12/2003 | Palmer et al. |
| 6,695,878 B2 | 2/2004 | McGuckin et al. |
| 6,783,538 B2 | 8/2004 | McGuckin et al. |
| 6,793,665 B2 | 9/2004 | McGuckin et al. |
| 6,890,340 B2 | 5/2005 | Duane |
| 6,932,831 B2 | 8/2005 | Forber |
| 6,958,074 B2 | 10/2005 | Russell |
| 6,972,025 B2 | 12/2005 | WasDyke |
| 6,989,021 B2 | 1/2006 | Bosma et al. |
| 6,994,092 B2 | 2/2006 | Va der Burg et al. |
| 7,037,321 B2 | 5/2006 | Sachdeva et al. |
| 7,097,651 B2 | 8/2006 | Harrison et al. |
| 7,232,462 B2 | 6/2007 | Schaeffer et al. |
| 7,279,000 B2 * | 10/2007 | Cartier et al. ................. 606/200 |
| 7,316,708 B2 | 1/2008 | Gordon et al. |
| 7,534,251 B2 | 5/2009 | WasDyke et al. |
| 7,572,289 B2 | 8/2009 | Sisken et al. |
| 7,867,245 B2 | 1/2011 | Neeman et al. |
| 7,875,018 B2 | 1/2011 | Tockman et al. |
| 7,998,164 B2 | 8/2011 | Saholt et al. |
| 2002/0058911 A1 | 5/2002 | Gilson et al. |
| 2002/0116024 A1 | 8/2002 | Goldberg et al. |
| 2002/0193827 A1 | 12/2002 | McGuckin et al. |
| 2002/0193828 A1 | 12/2002 | Griffin et al. |
| 2003/0130680 A1 | 7/2003 | Russell |
| 2003/0195555 A1 | 10/2003 | Khairkhahan et al. |
| 2003/0208227 A1 | 11/2003 | Thomas |
| 2003/0208253 A1 | 11/2003 | Beyer et al. |
| 2004/0044361 A1 | 3/2004 | Frazier et al. |
| 2004/0073252 A1 | 4/2004 | Goldberg et al. |
| 2004/0093017 A1 | 5/2004 | Chanduszko |

| | | |
|---|---|---|
| 2004/0158273 A1 | 8/2004 | Weaver et al. |
| 2004/0186510 A1 | 9/2004 | Weaver |
| 2004/0186556 A1 | 9/2004 | Hogendijk et al. |
| 2004/0215230 A1 | 10/2004 | Frazier et al. |
| 2004/0230220 A1 | 11/2004 | Osborne |
| 2005/0004596 A1 | 1/2005 | McGuckin et al. |
| 2005/0015111 A1 | 1/2005 | McGuckin et al. |
| 2005/0027314 A1 | 2/2005 | WasDyke |
| 2005/0043757 A1 | 2/2005 | Arad et al. |
| 2005/0165442 A1* | 7/2005 | Thinnes et al. ............... 606/200 |
| 2005/0182439 A1 | 8/2005 | Lowe |
| 2005/0234503 A1 | 10/2005 | Ravenscroft et al. |
| 2005/0251199 A1 | 11/2005 | Osborne et al. |
| 2005/0267514 A1 | 12/2005 | Osborne et al. |
| 2005/0277977 A1 | 12/2005 | Thornton |
| 2005/0288704 A1 | 12/2005 | Cartier et al. |
| 2006/0030875 A1 | 2/2006 | Tessmer |
| 2006/0058832 A1 | 3/2006 | Melzer et al. |
| 2006/0079928 A1* | 4/2006 | Cartier et al. ................. 606/200 |
| 2006/0079930 A1 | 4/2006 | McGuckin, Jr. et al. |
| 2006/0095068 A1 | 5/2006 | WasDyke et al. |
| 2006/0100660 A1 | 5/2006 | Osborne et al. |
| 2006/0106417 A1 | 5/2006 | Tessmer et al. |
| 2006/0149295 A1 | 7/2006 | Fleming, III |
| 2006/0167490 A1 | 7/2006 | Kusleika et al. |
| 2006/0178695 A1 | 8/2006 | Decant et al. |
| 2006/0206138 A1 | 9/2006 | Eidenschink |
| 2007/0005095 A1 | 1/2007 | Osborne et al. |
| 2007/0032816 A1 | 2/2007 | O'Connell et al. |
| 2007/0088381 A1 | 4/2007 | McGuckin, Jr. et al. |
| 2007/0167974 A1 | 7/2007 | Cully et al. |
| 2007/0173885 A1 | 7/2007 | Cartier et al. |
| 2007/0198050 A1 | 8/2007 | Ravenscroft et al. |
| 2007/0213685 A1 | 9/2007 | Bressler et al. |
| 2008/0188887 A1* | 8/2008 | Batiste .......................... 606/200 |
| 2008/0275486 A1* | 11/2008 | Dwyer et al. ................. 606/200 |
| 2009/0198270 A1 | 8/2009 | McGuckin et al. |
| 2010/0049238 A1 | 2/2010 | Simpson |
| 2010/0063535 A1 | 3/2010 | Bressler et al. |
| 2010/0106178 A1 | 4/2010 | Obermiller et al. |

FOREIGN PATENT DOCUMENTS

| | | |
|---|---|---|
| WO | WO 9509567 | 4/1995 |
| WO | WO 9925252 | 5/1999 |
| WO | WO 0110342 | 2/2001 |
| WO | WO 0445590 | 6/2001 |
| WO | WO 0162184 | 8/2001 |
| WO | WO 0172239 | 10/2001 |
| WO | 0211812 | 2/2002 |
| WO | WO 0232496 | 4/2002 |
| WO | WO 03063732 | 8/2003 |
| WO | WO 2004049973 | 6/2004 |
| WO | WO 2005117750 | 12/2005 |
| WO | WO 2006036457 | 4/2006 |

OTHER PUBLICATIONS

Gianturco-Roehm, Bird's Nest® Vena Cava Filter.

Cordis Corporation, TrapEase™ Permanent Vena Cava Filter, "A Small, Easy and Verstaile System for Optimal Pulmonary Emboli Prevention", 2000 (4 pages).

* cited by examiner

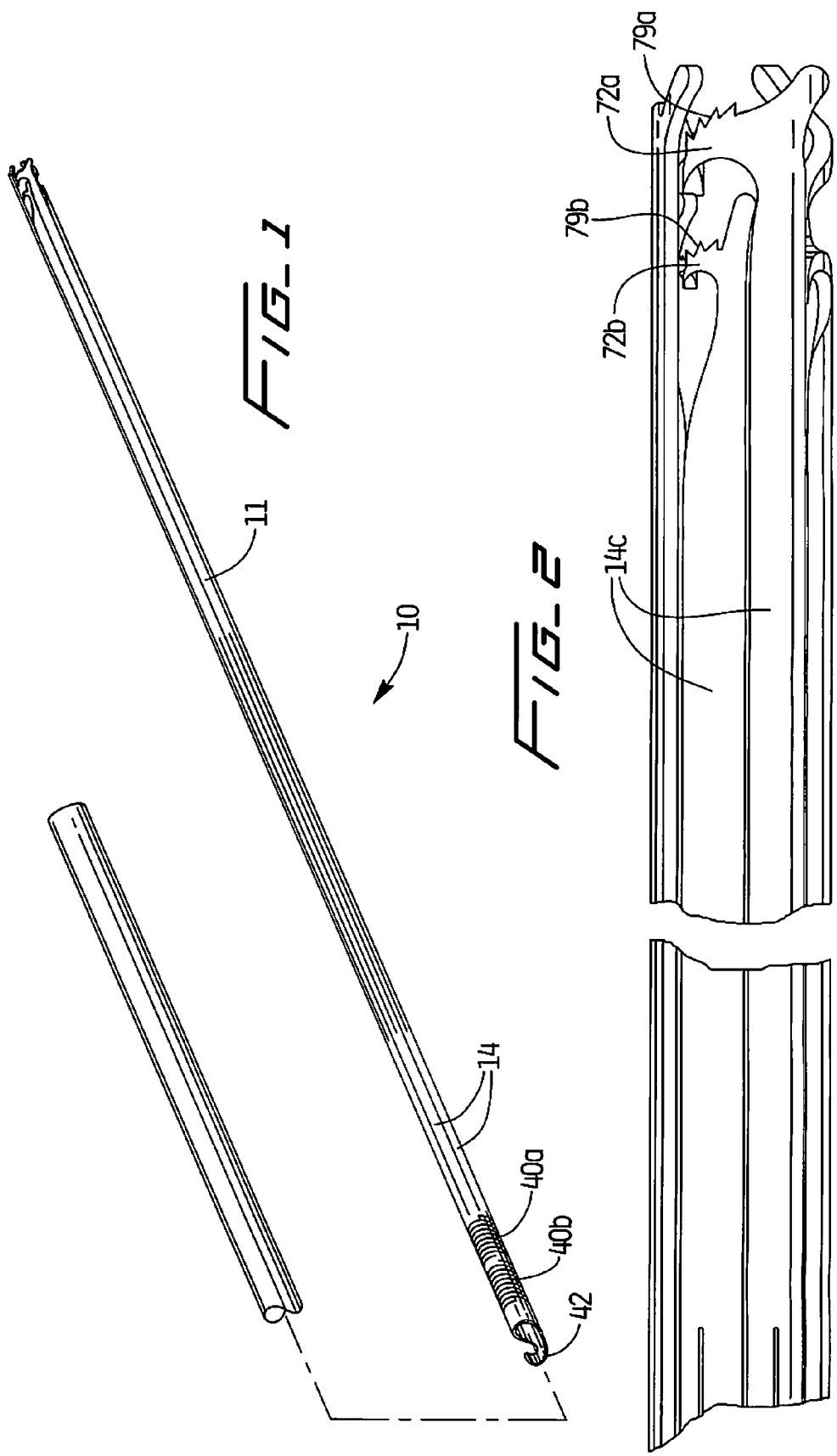

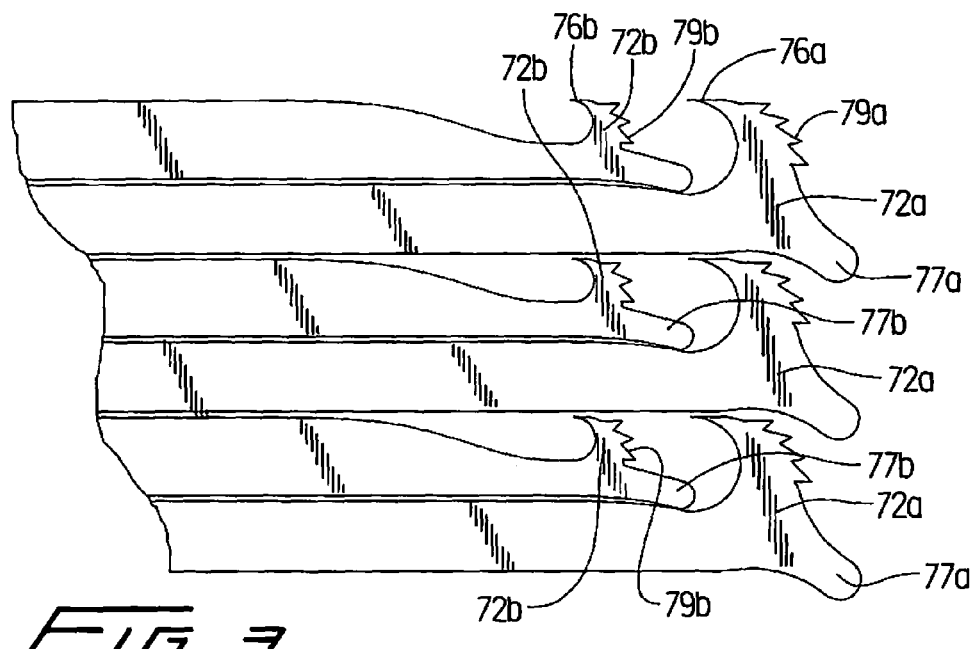
FIG_3
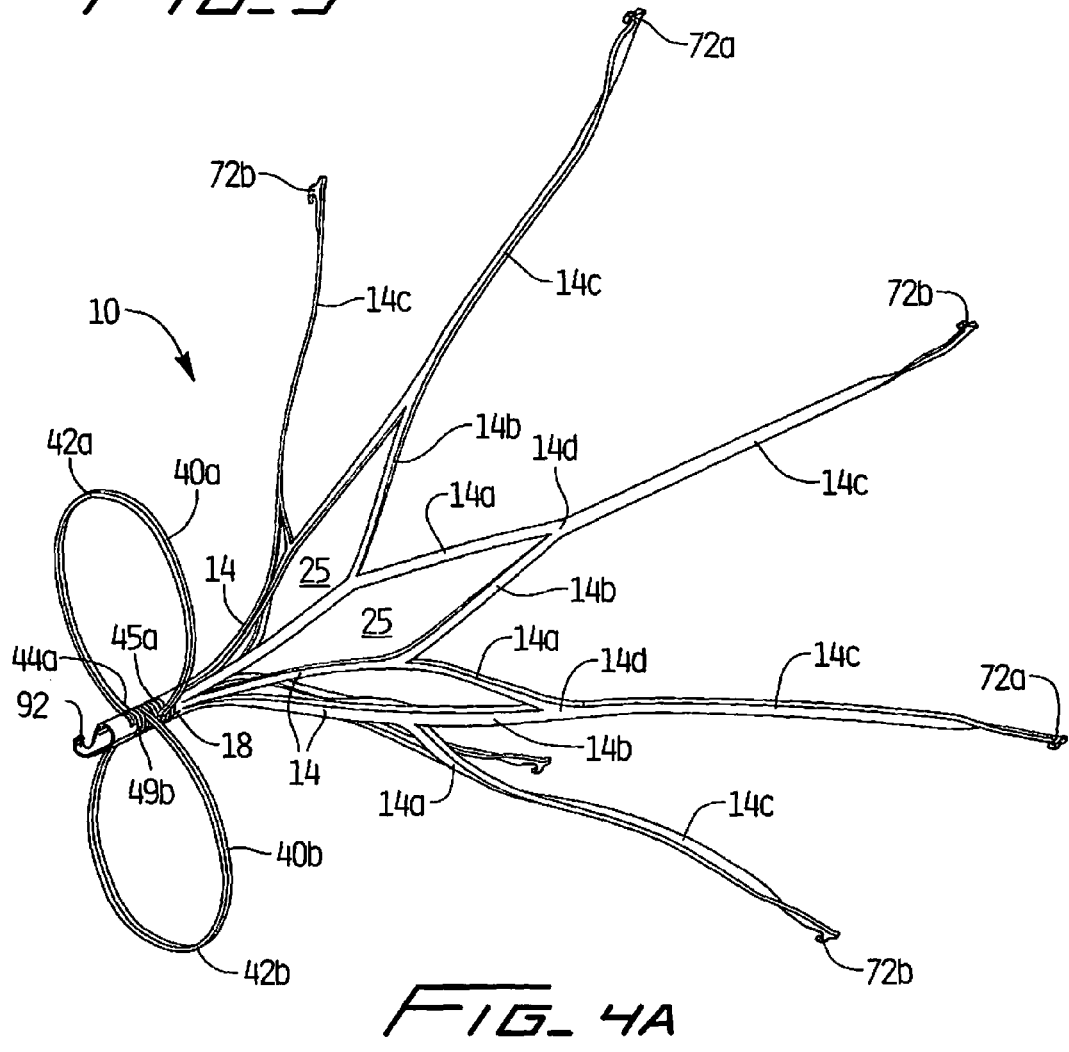
FIG_4A

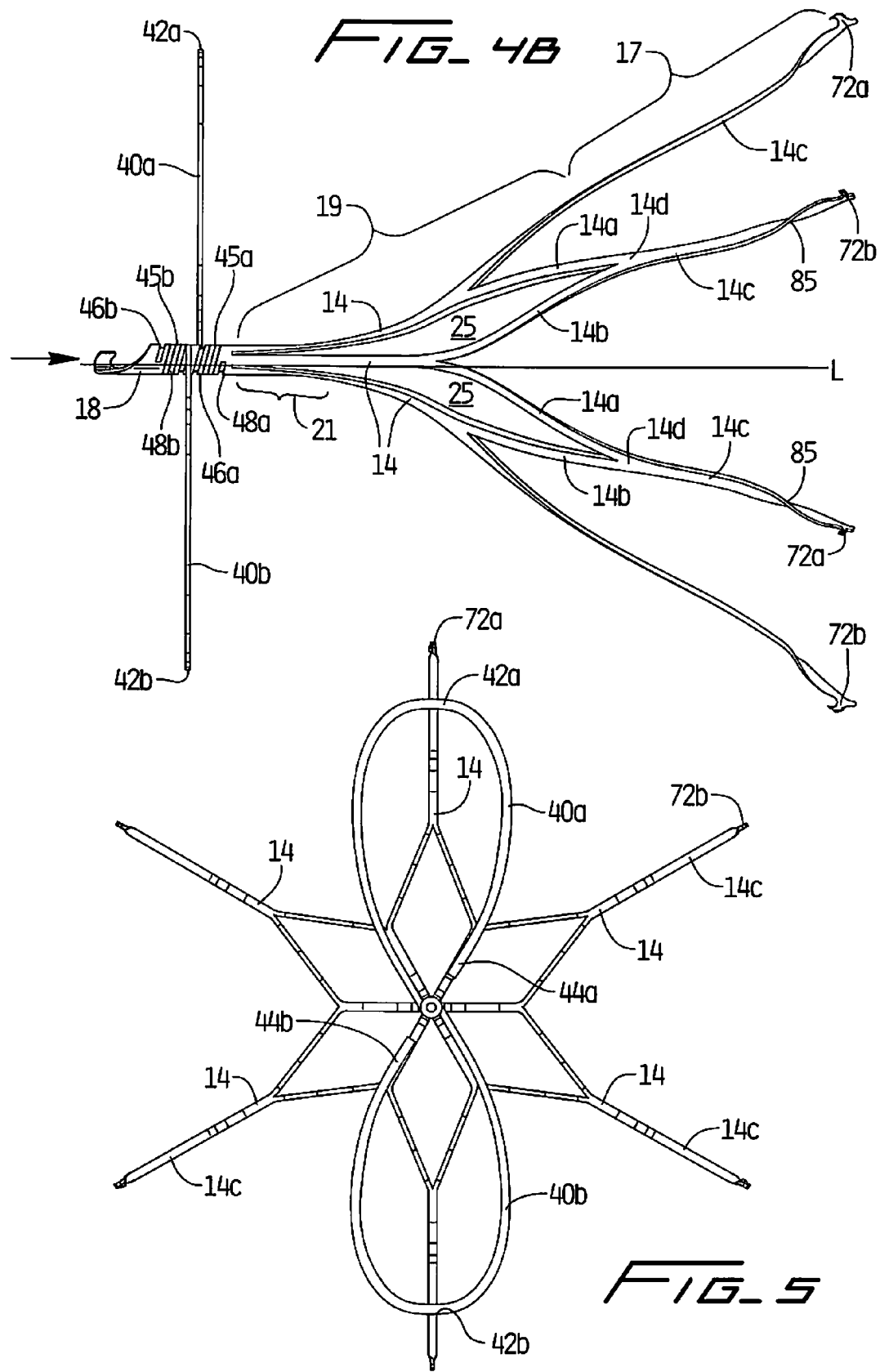

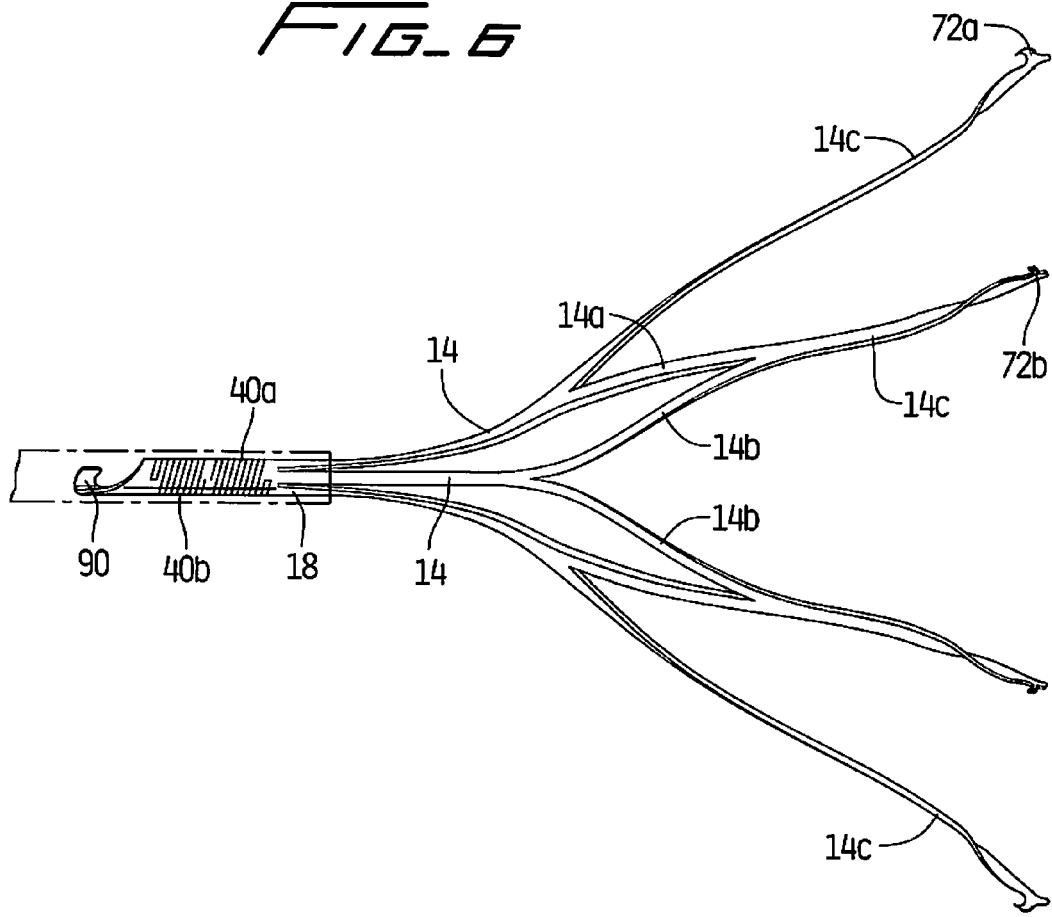
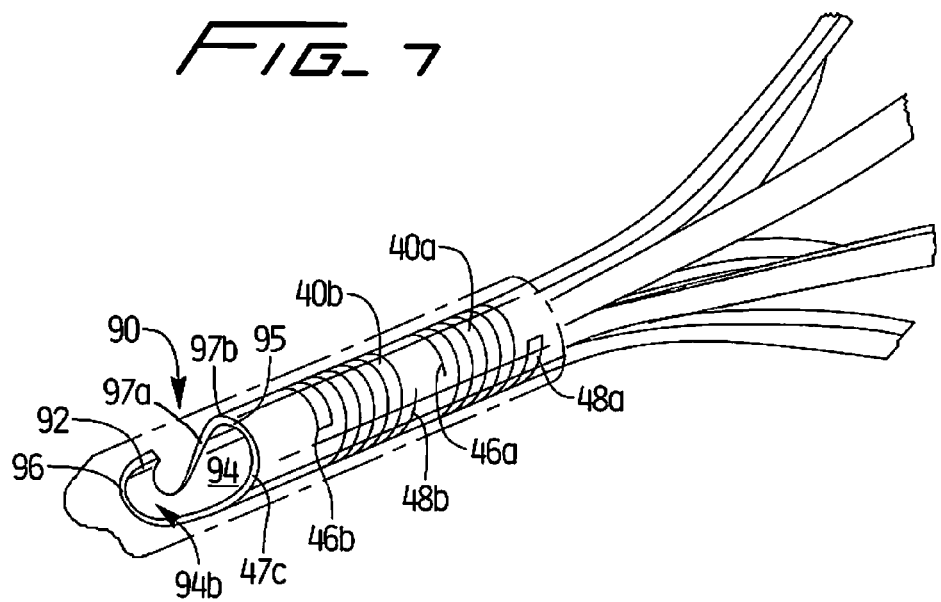

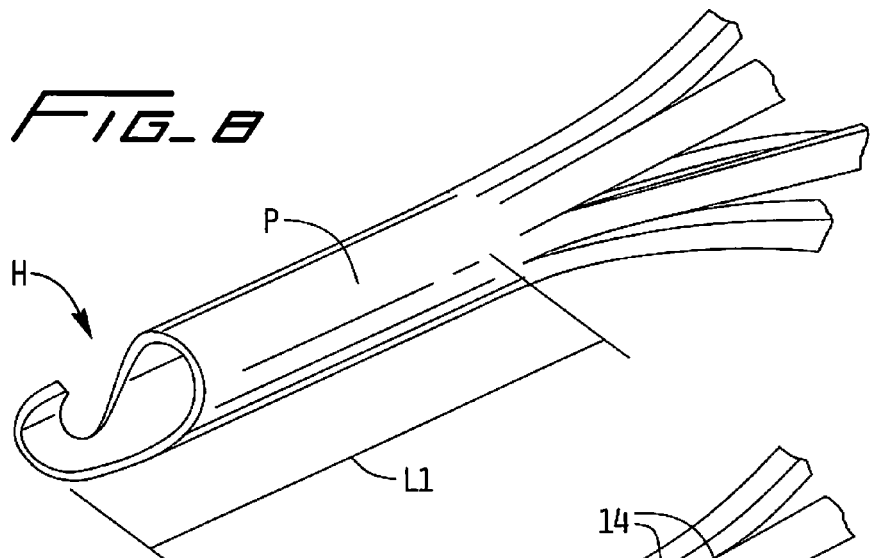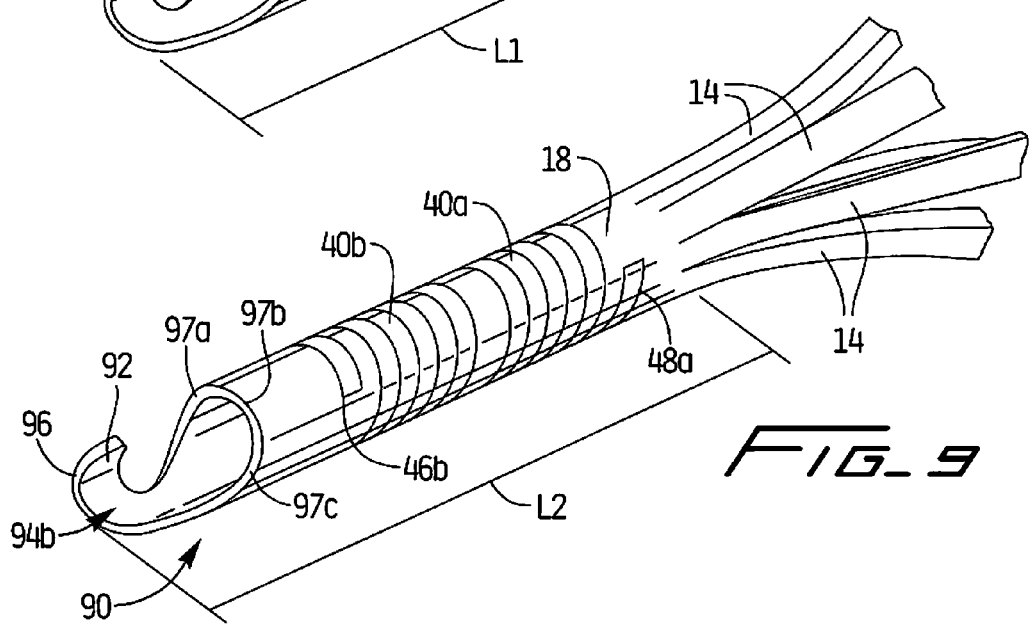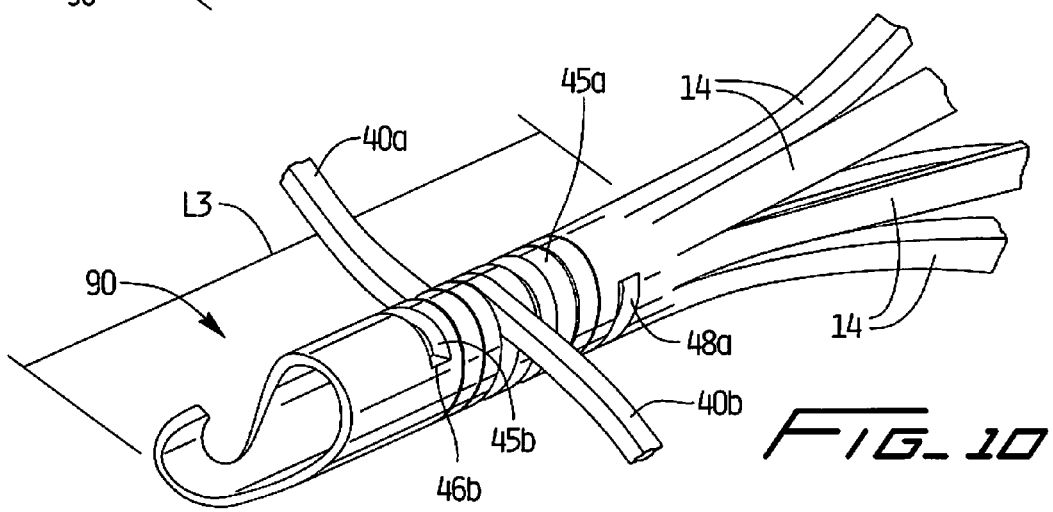

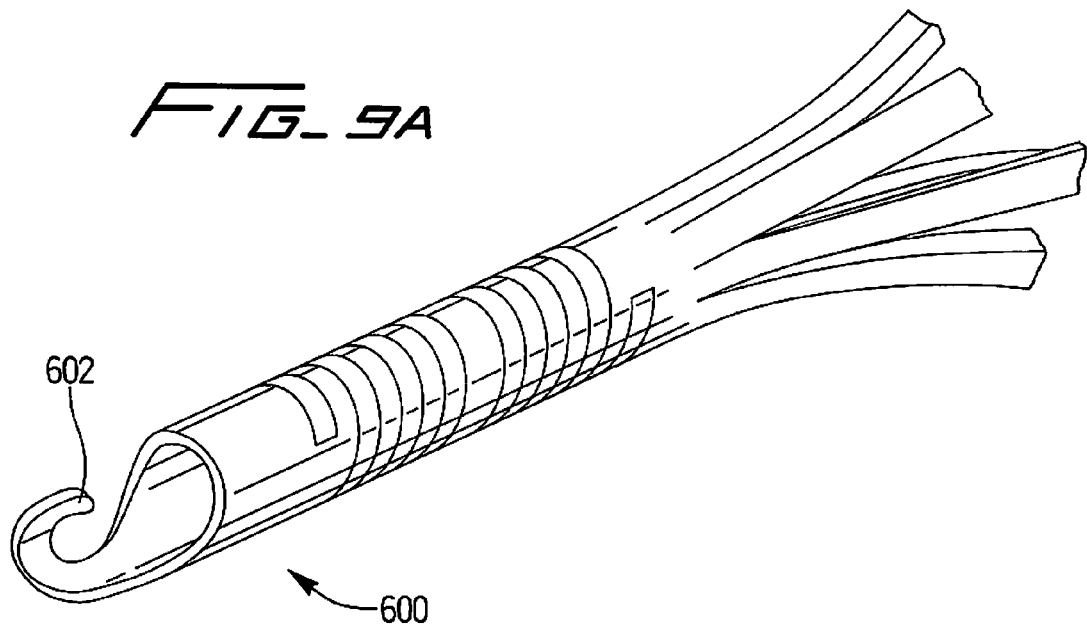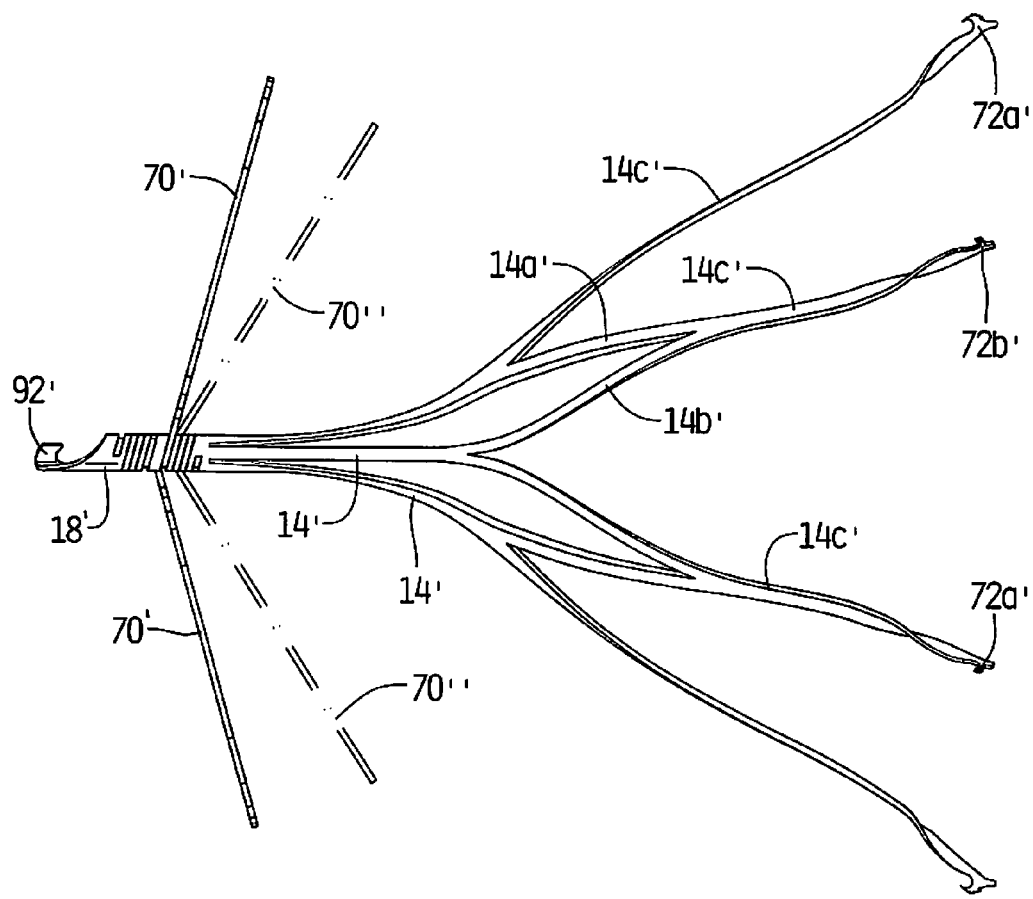

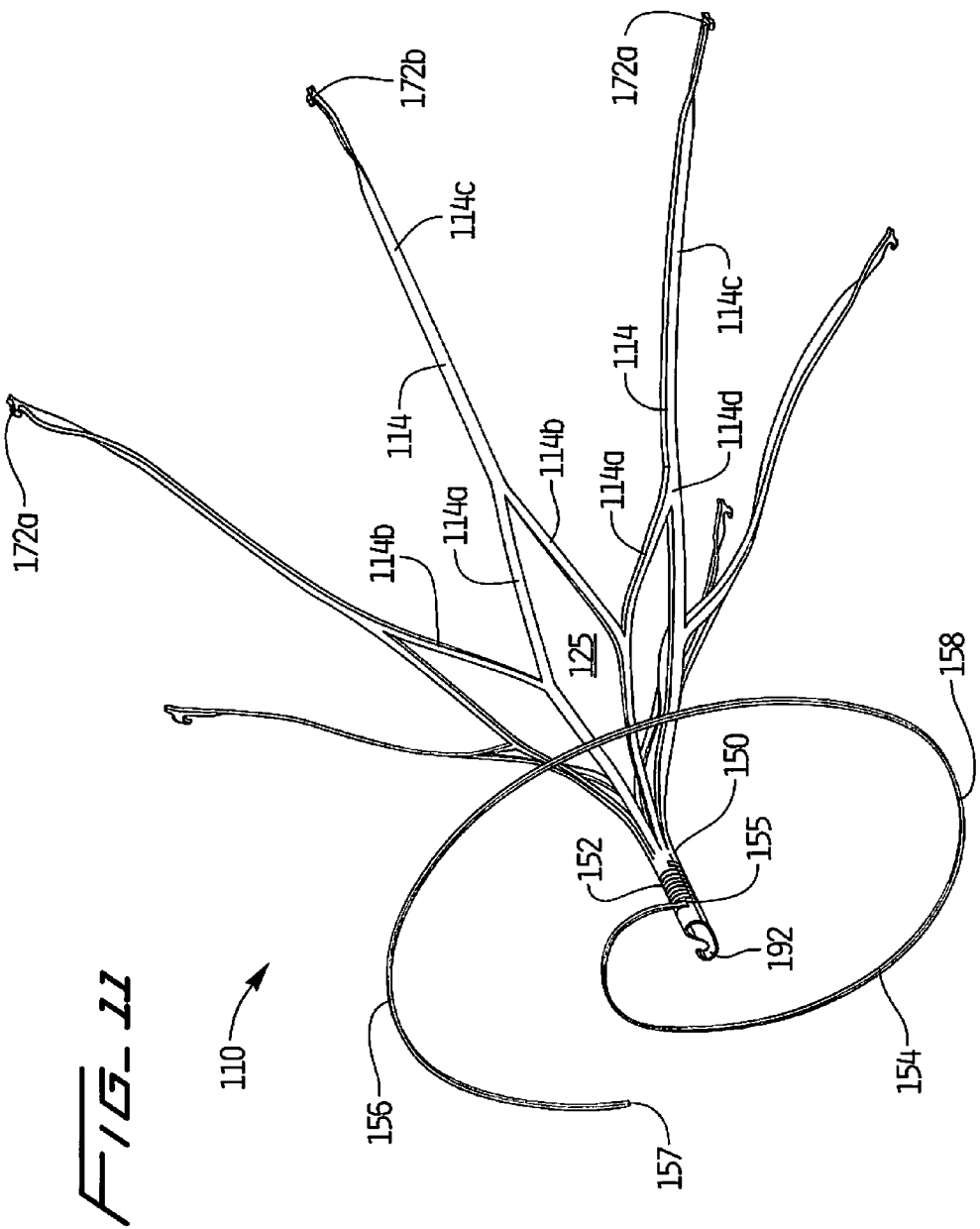

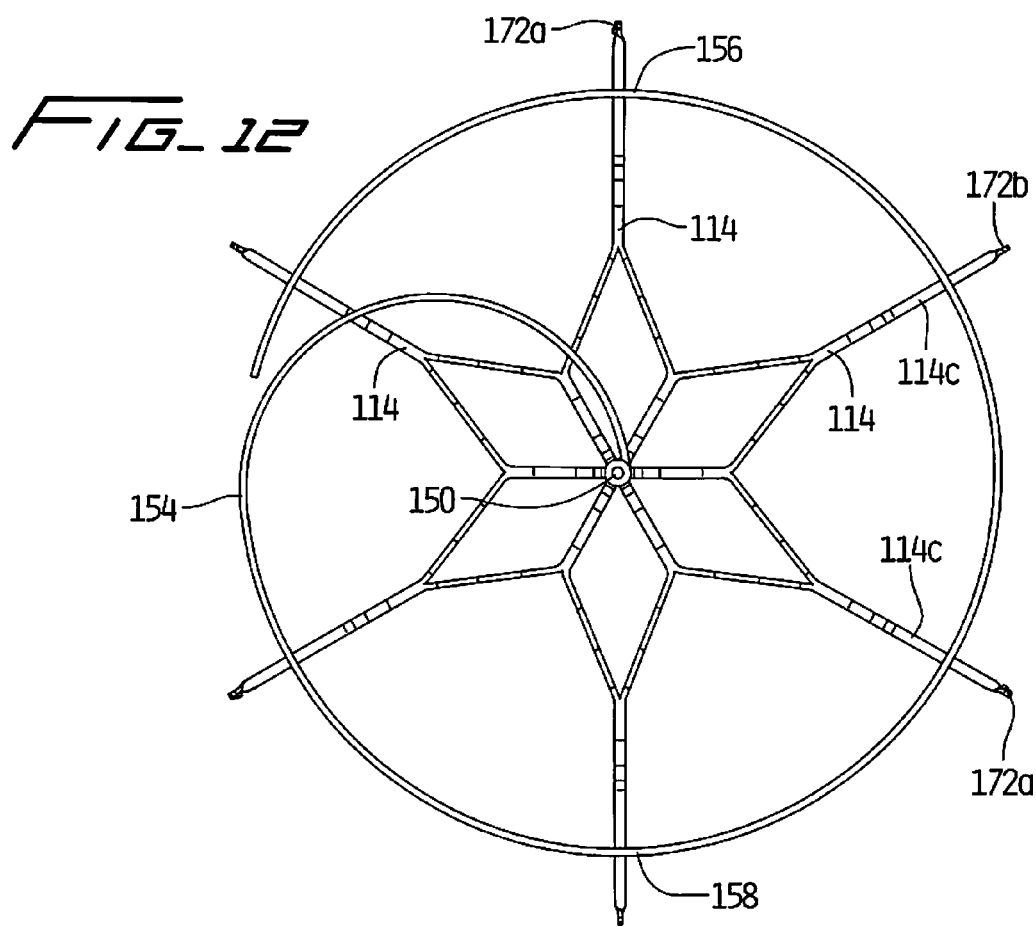
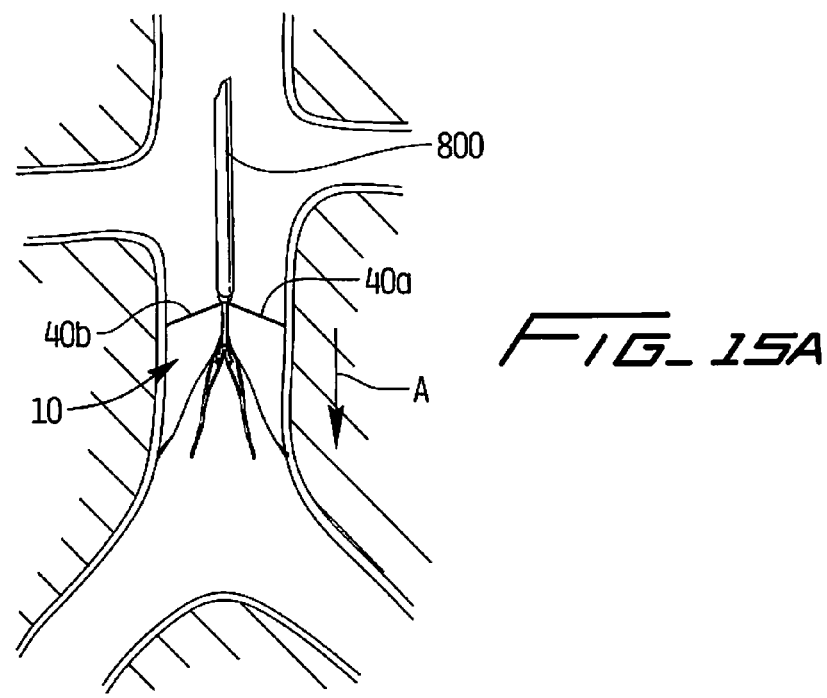

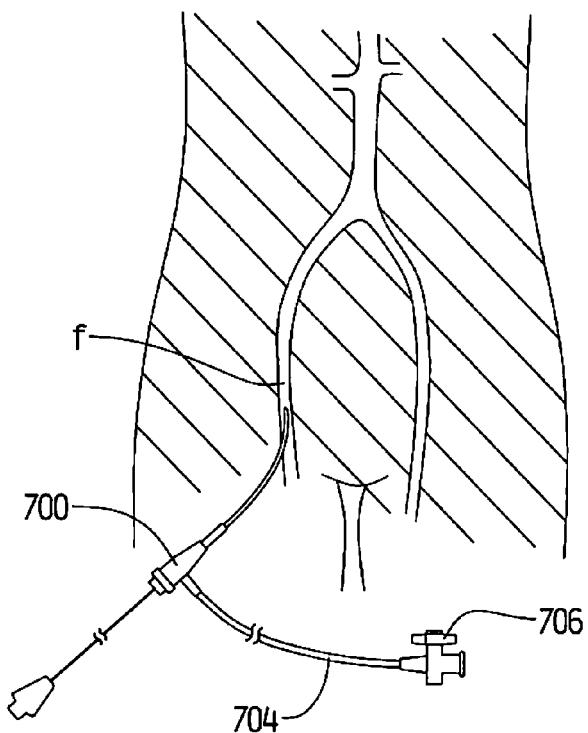
FIG_13
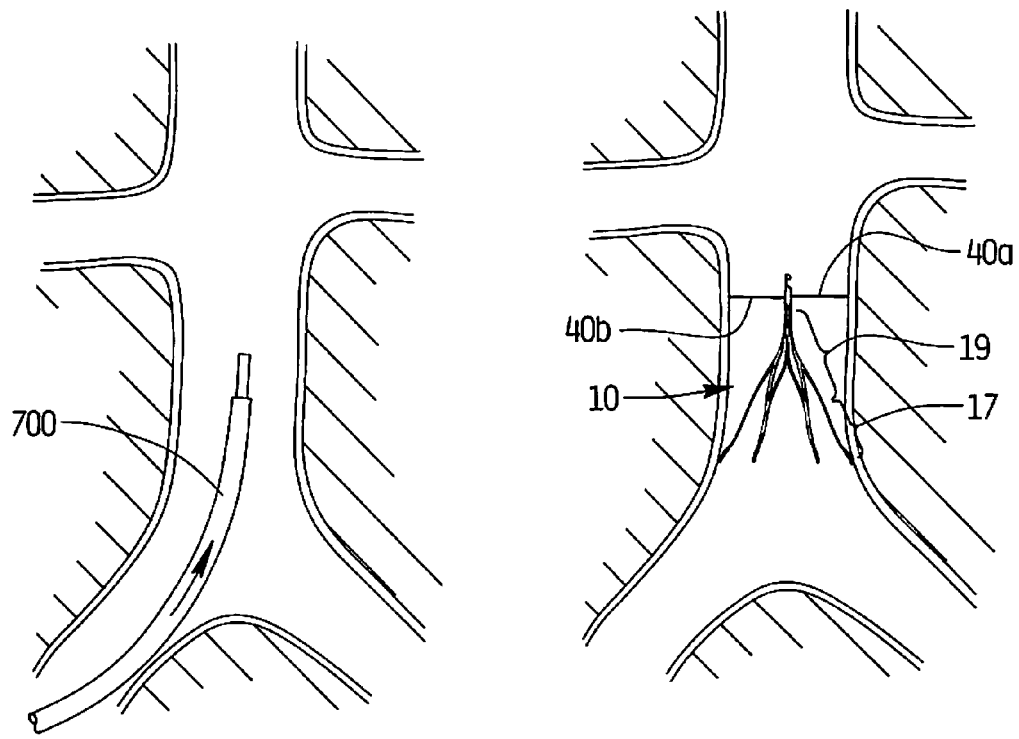
FIG_14
FIG_15

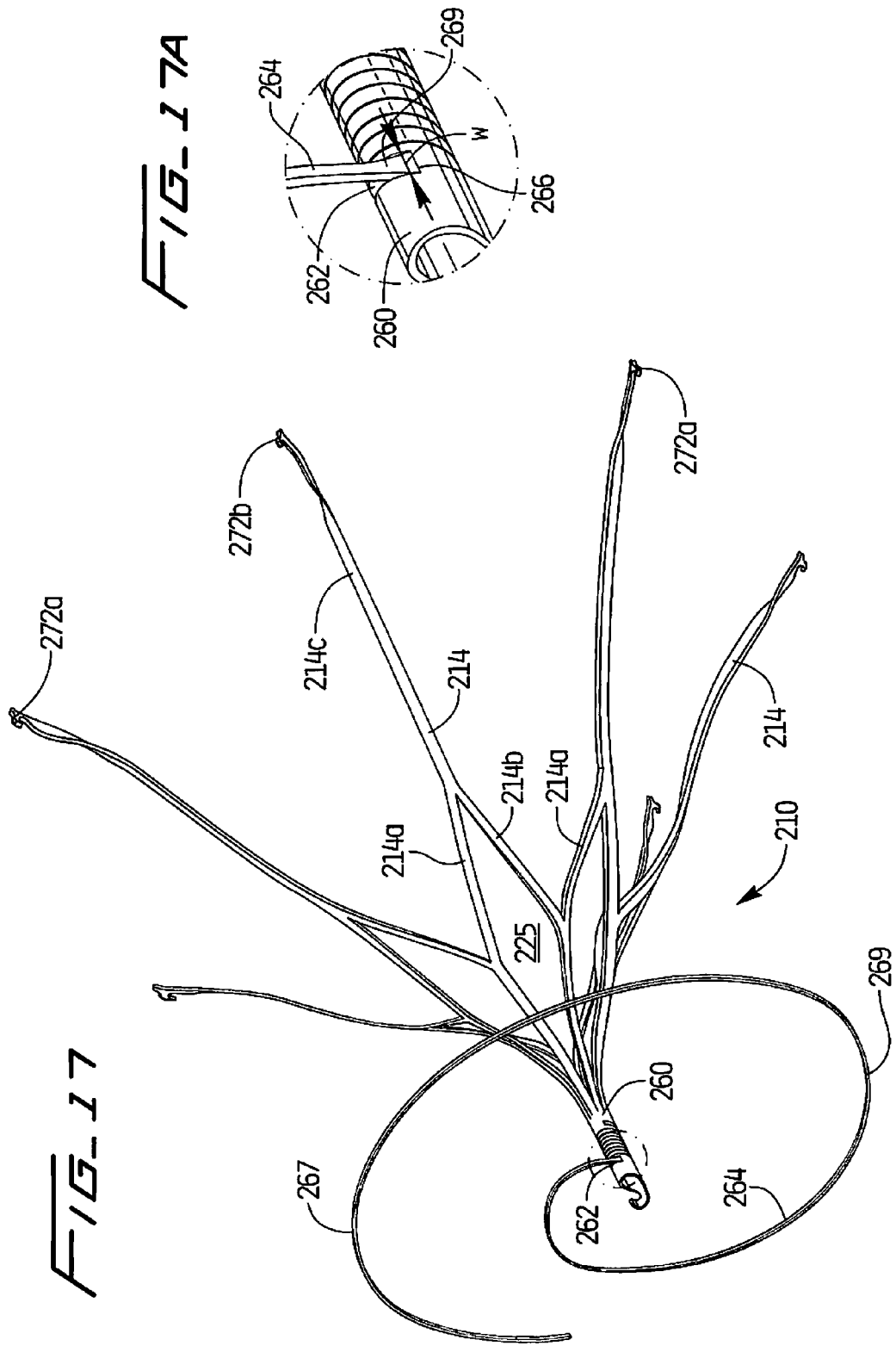

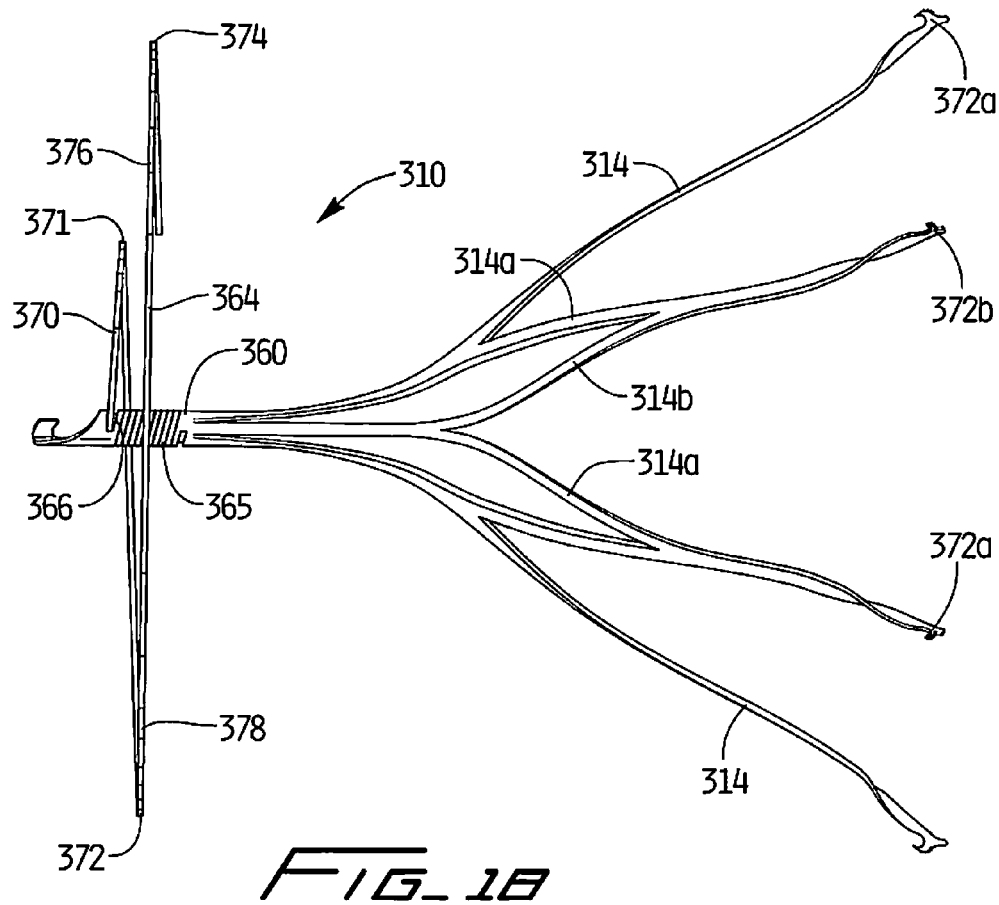
FIG_18
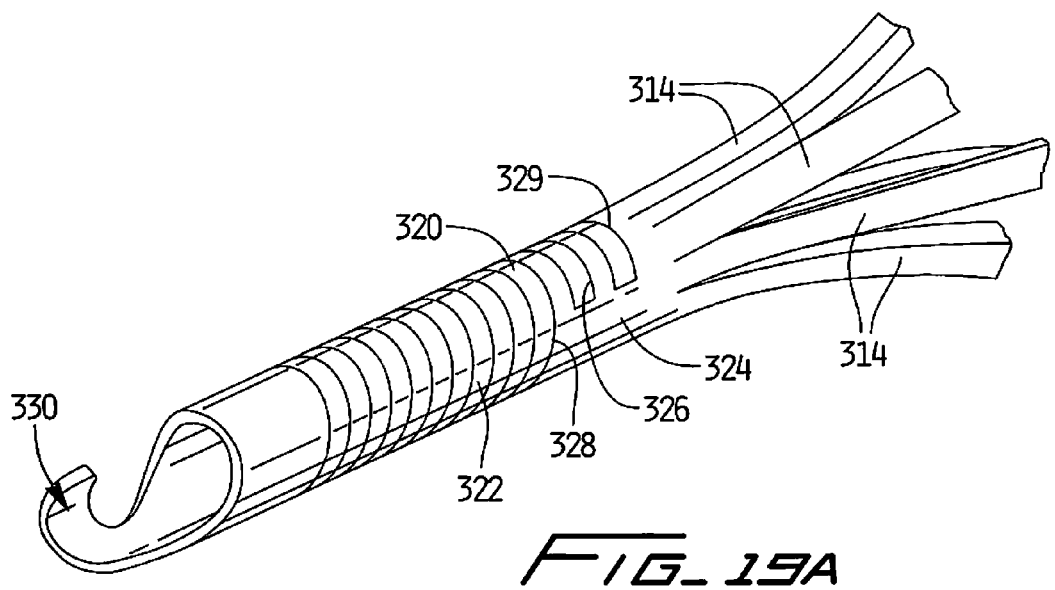
FIG_19A

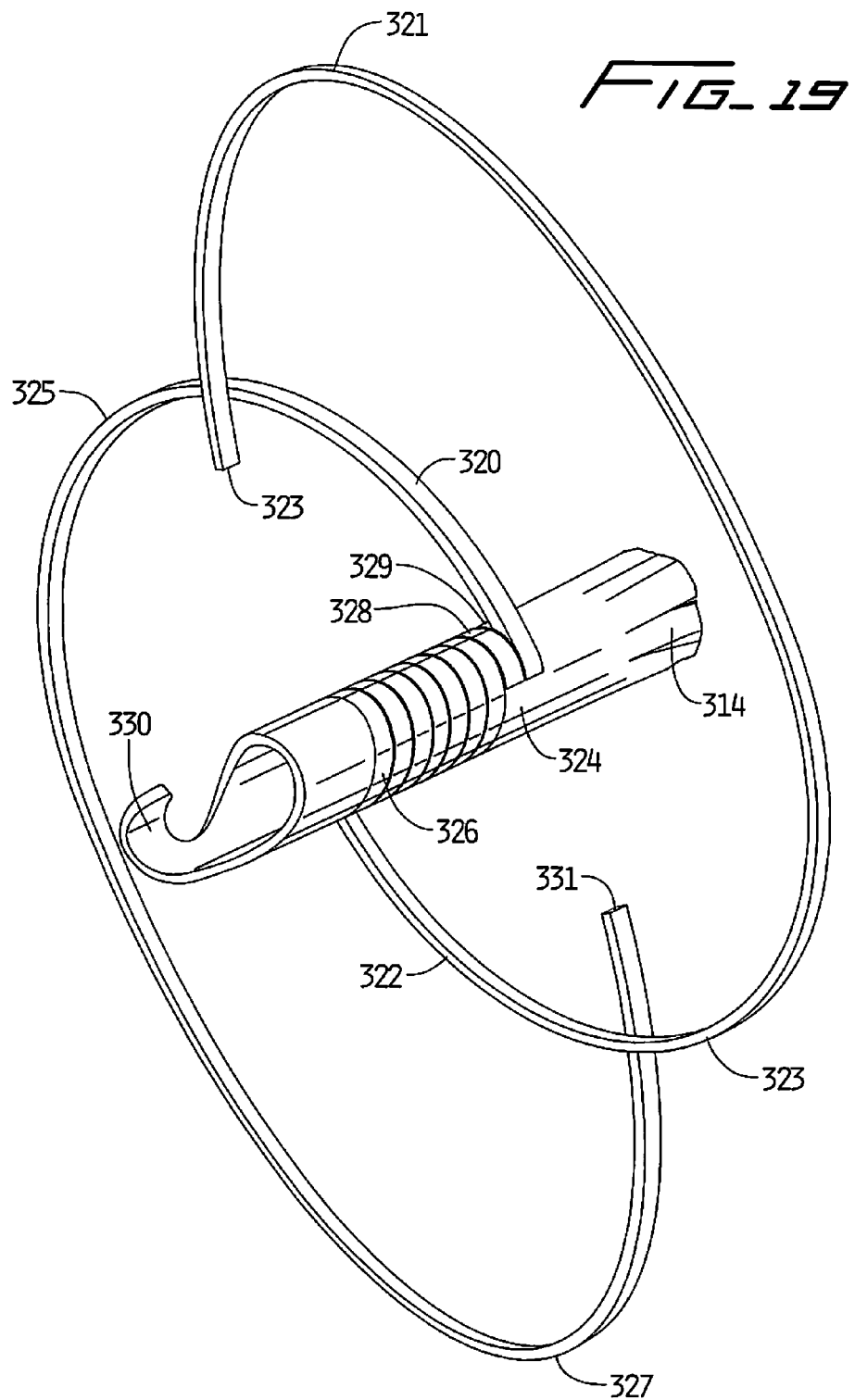

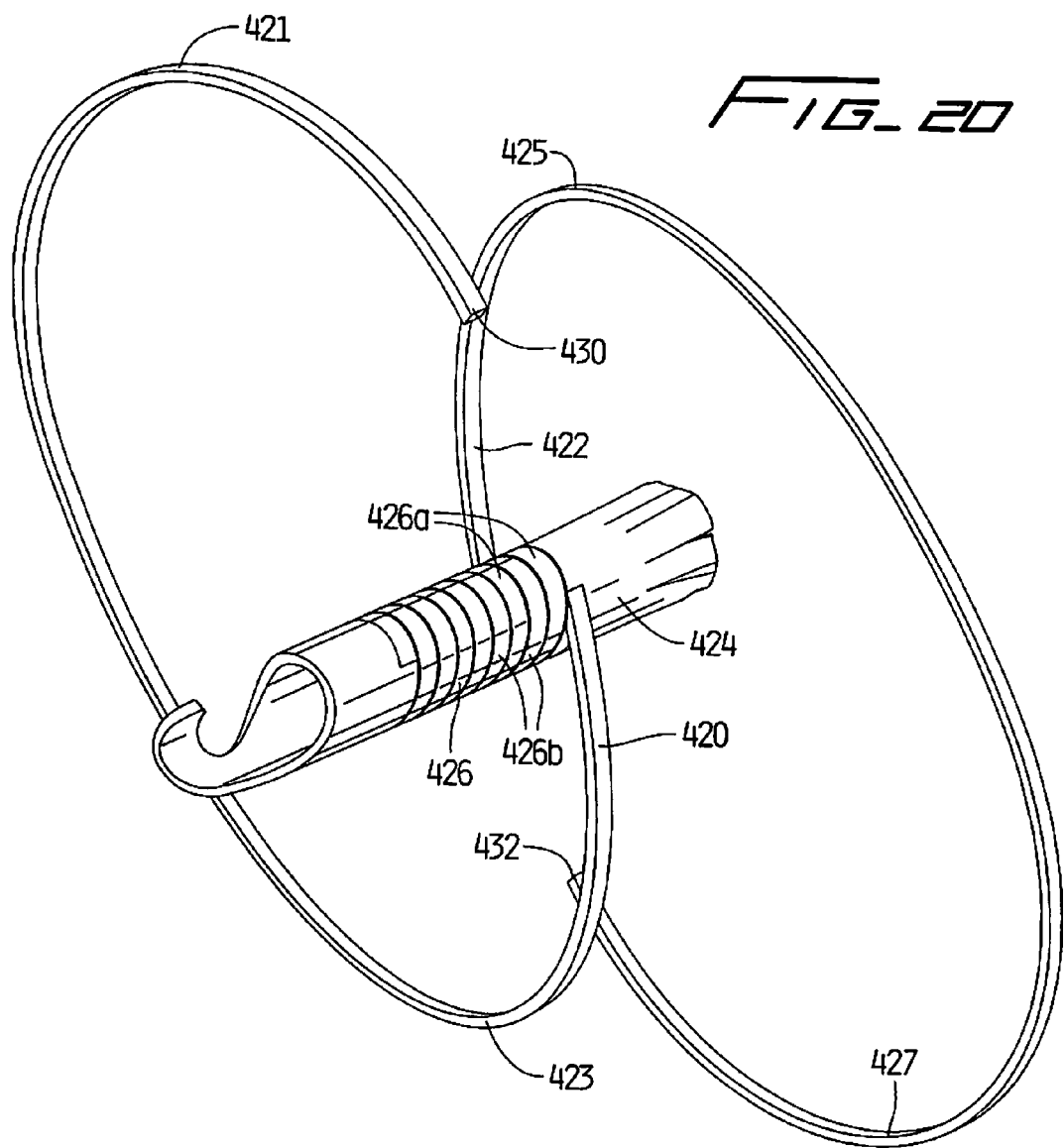
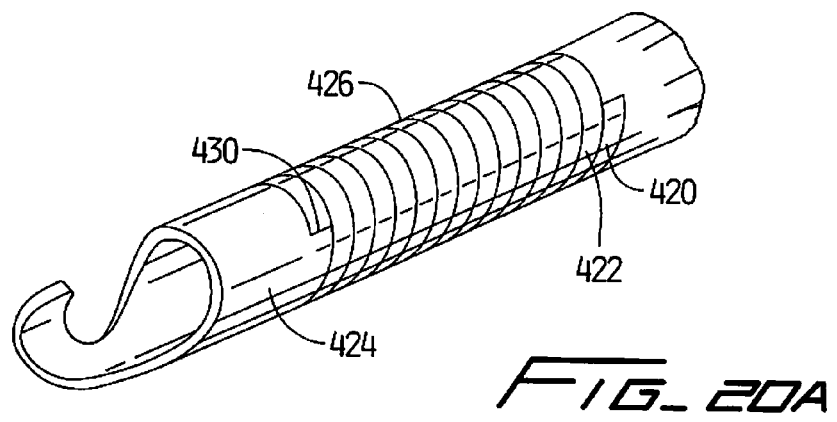

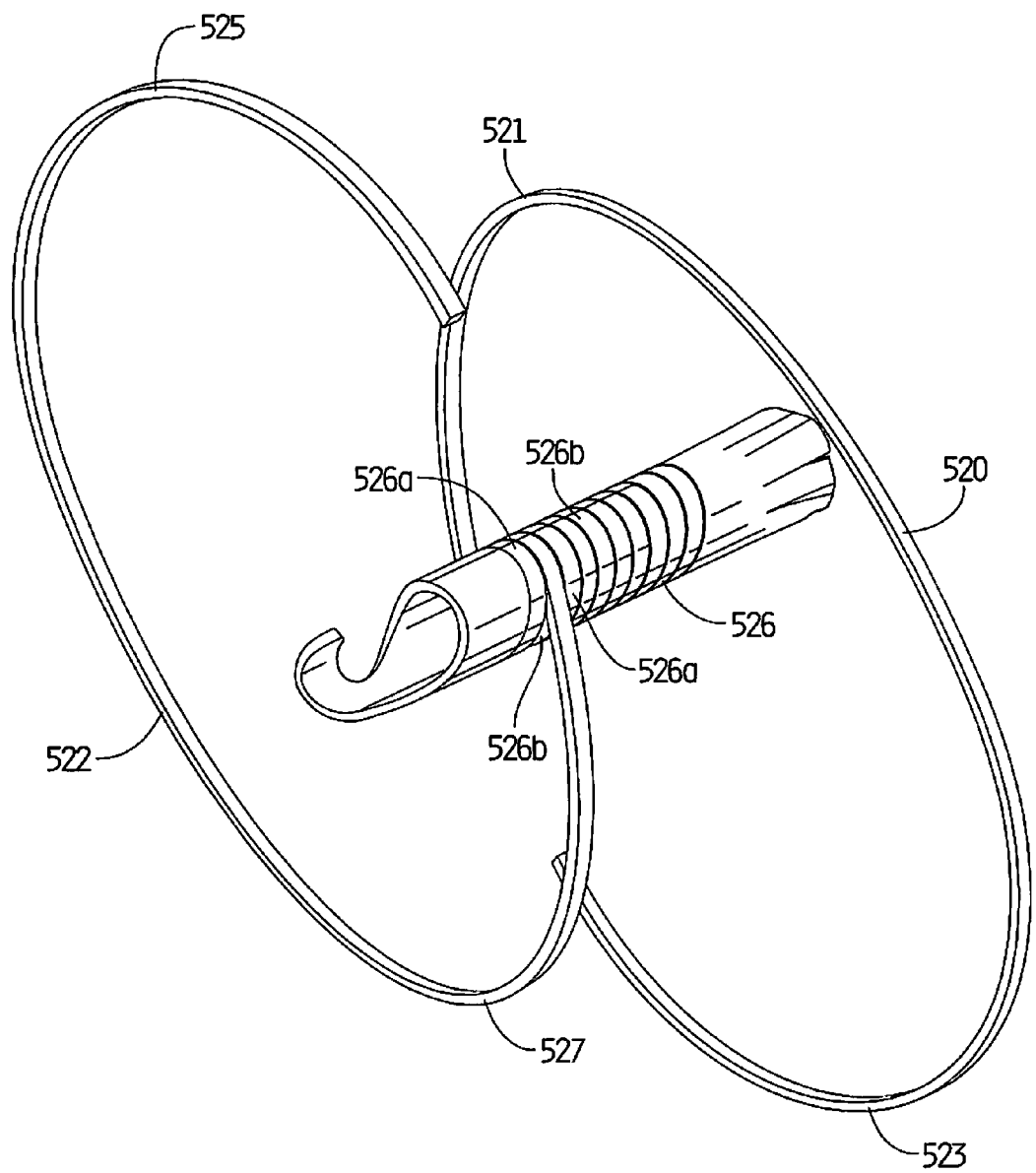
FIG_21

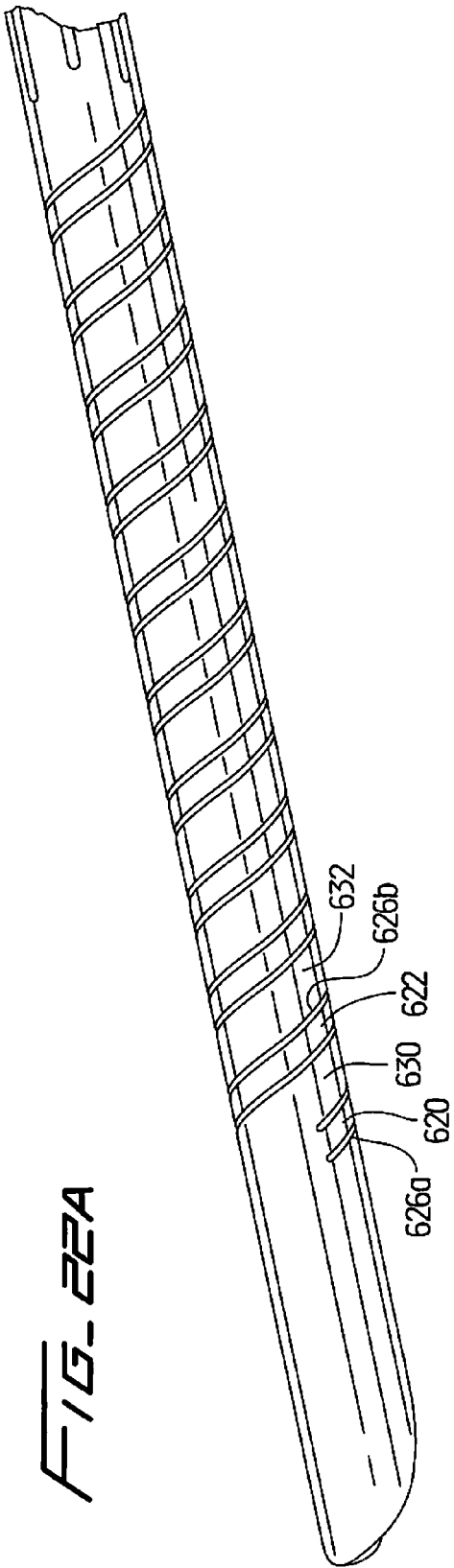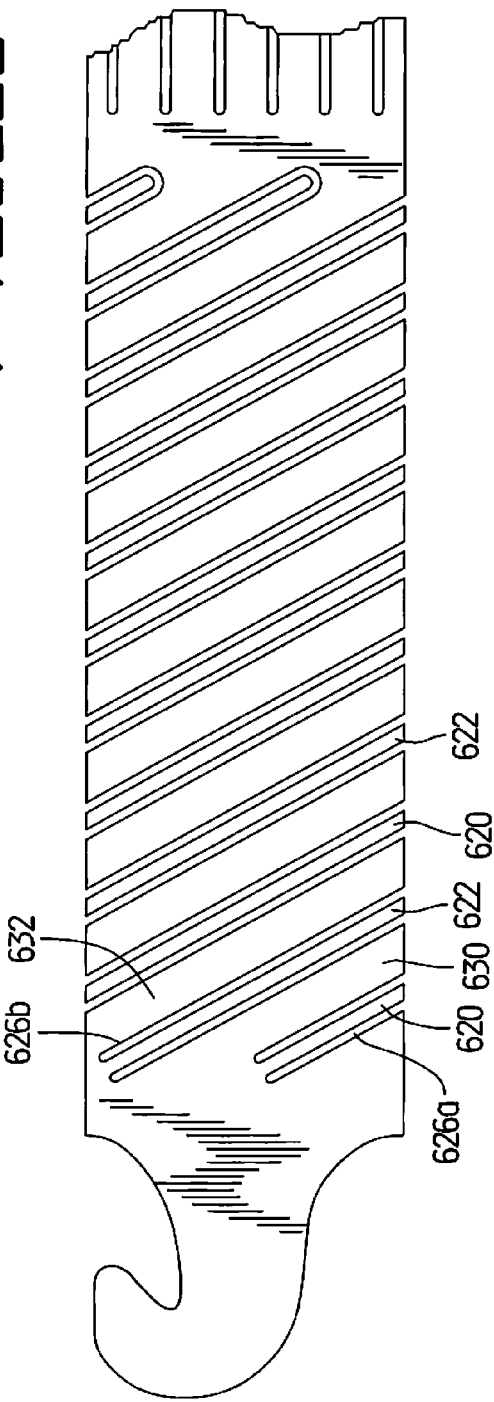

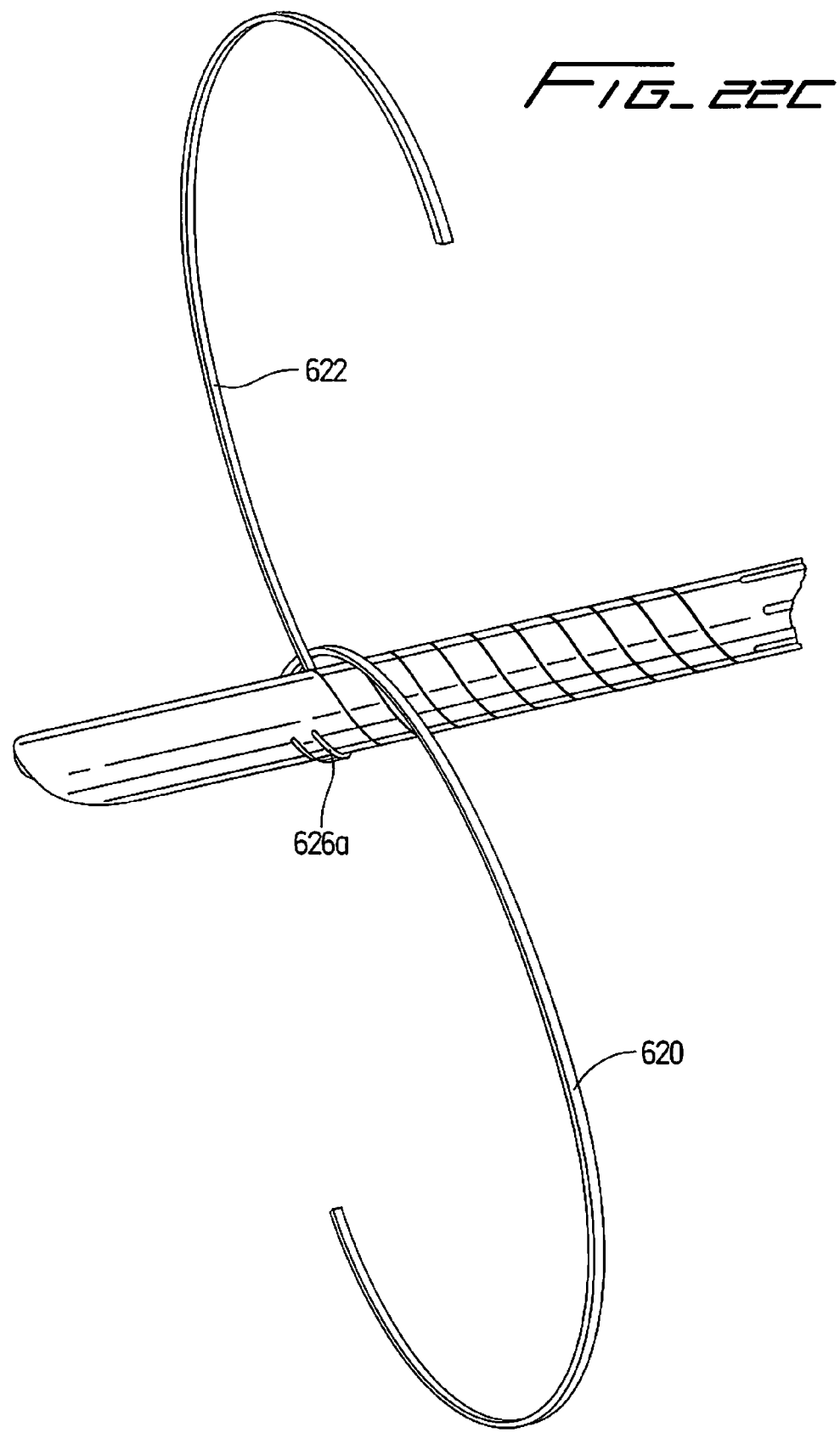

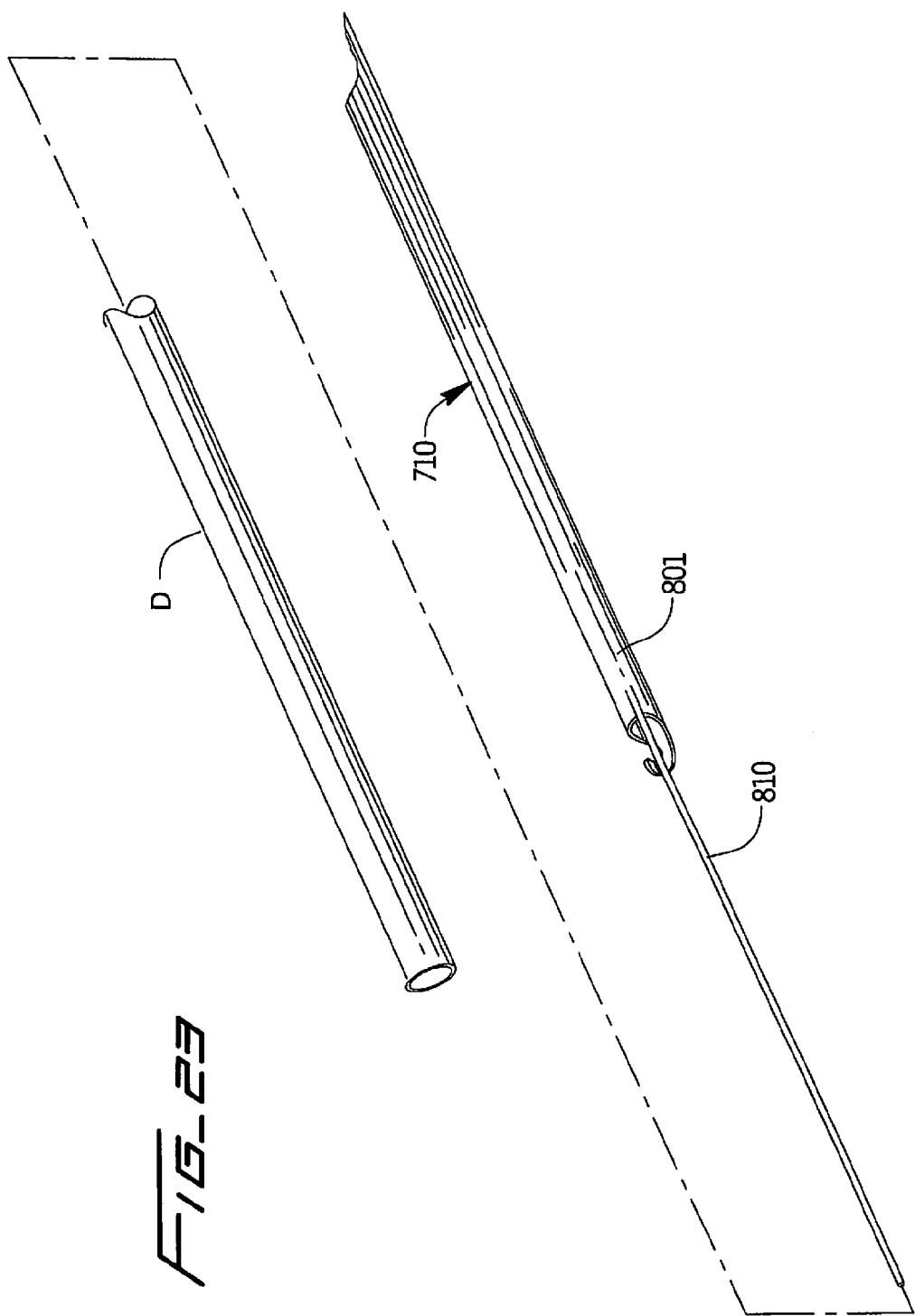

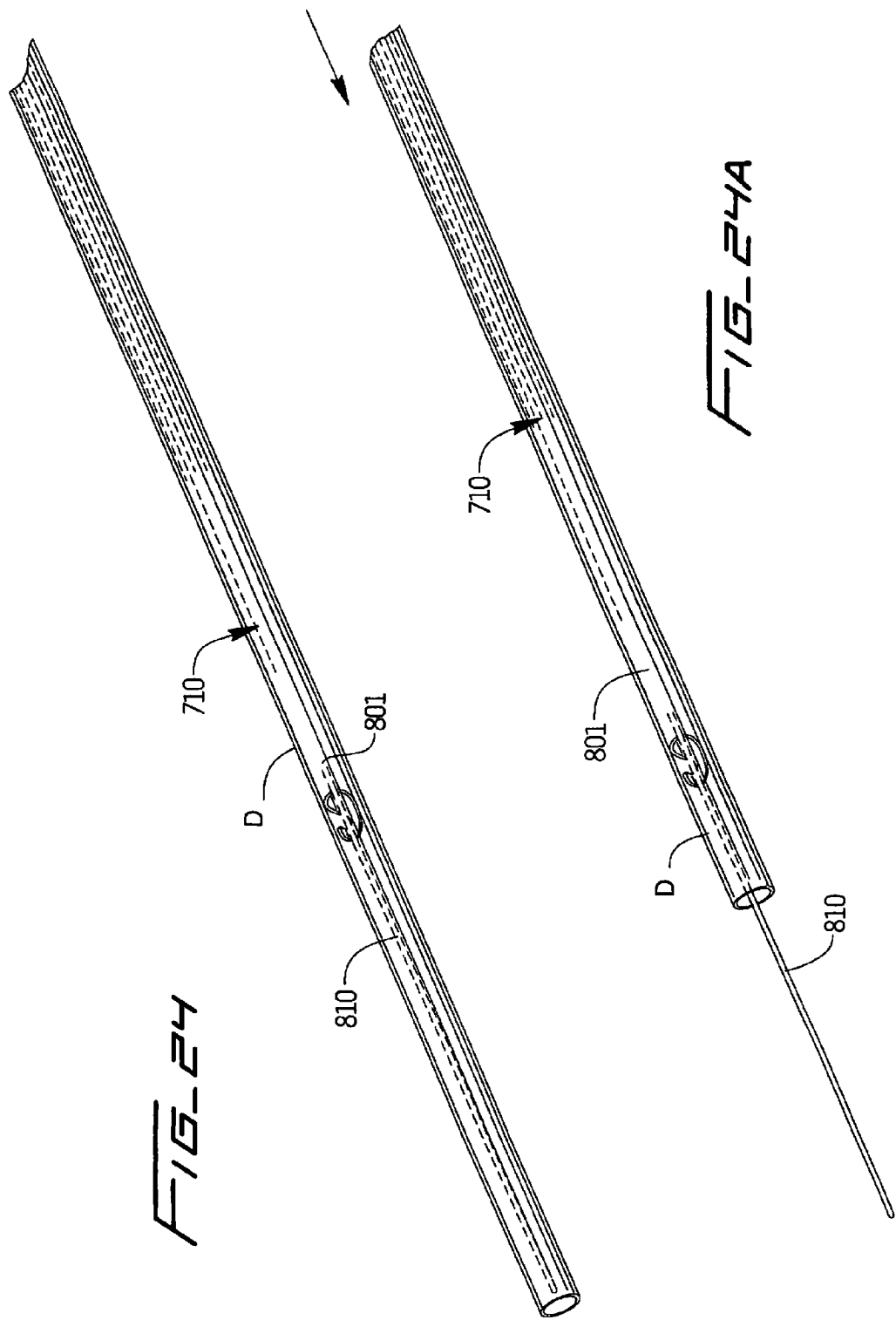

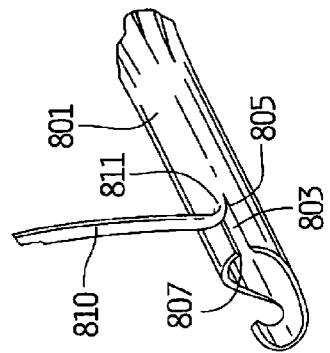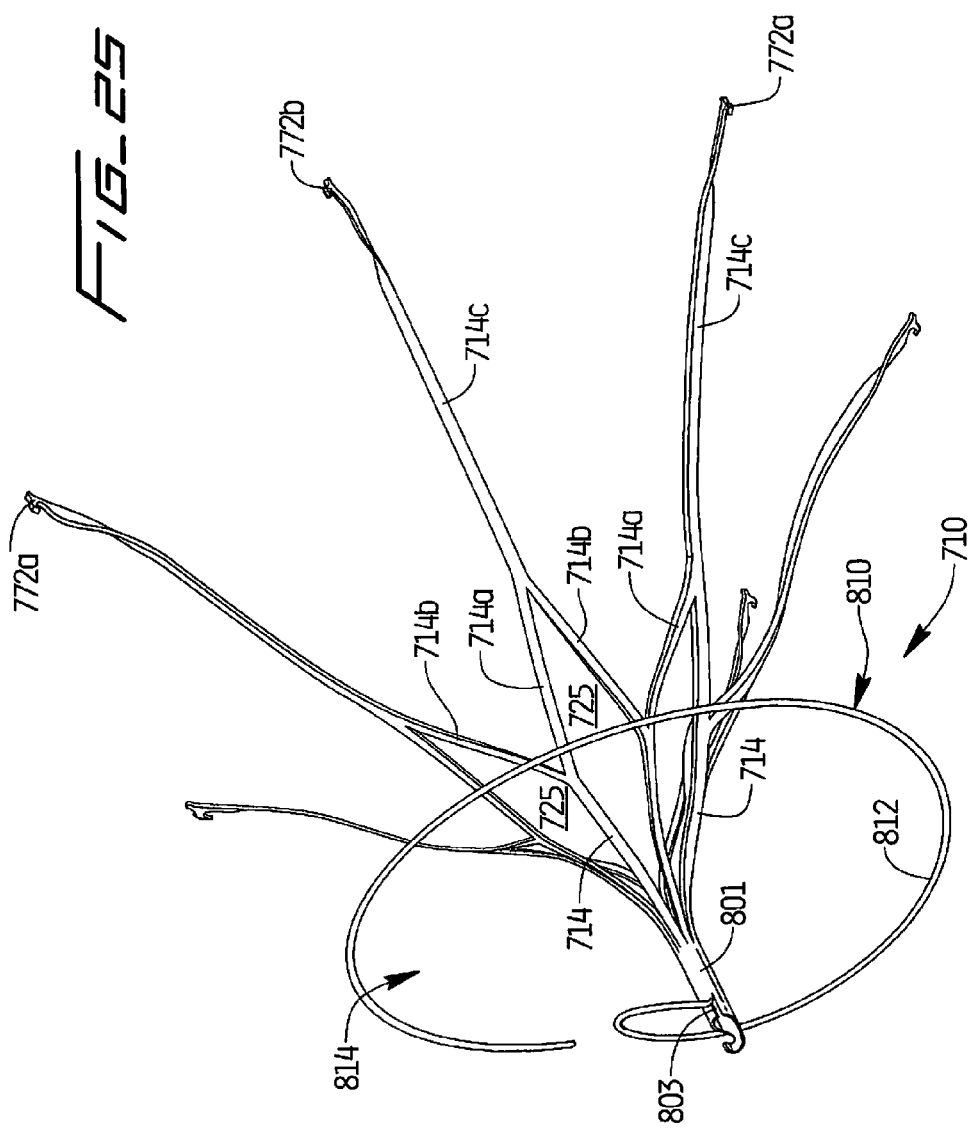

VEIN FILTER

This application claims priority from provisional application 61/191,903, filed Sep. 12, 2008 and is a continuation-in-part of application Ser. No. 11/888,929, now U.S. Pat. No. 8,062,236 filed Aug. 3, 2007, which claims priority from provisional application Ser. No. 60/840,888, filed Aug. 29, 2006 and is a continuation-in-part of application Ser. No. 10/889,429, now U.S. Pat. No. 7,704,266, filed Jul. 12, 2004, which claims priority from provisional application Ser. No. 60/572,274, filed May 18, 2004, and is a continuation-in-part of application Ser. No. 10/805,796, now U.S. Pat. No. 7,338,512, filed Mar. 22, 2004, which claims priority from provisional application Ser. No. 60/538,379, filed Jan. 22, 2004. The entire contents of each of these applications are incorporated herein by reference.

BACKGROUND

1. Technical Field

This application relates to a vascular filter and more particularly to a vein filter for capturing blood clots within the vessel.

2. Background of Related Art

Passage of blood clots to the lungs is known as pulmonary embolism. These clots typically originate in the veins of the lower limbs and can migrate through the vascular system to the lungs where they can obstruct blood flow and therefore interfere with oxygenation of the blood. Pulmonary embolisms can also cause shock and even death.

In some instances, blood thinning medication, e.g. anticoagulants such as Heparin, or sodium warfarin can be given to the patient. These medications, however, have limited use since they may not be able to be administered to patients after surgery or stroke or given to patients with high risk of internal bleeding. Also, this medication approach is not always effective in preventing recurring blood clots.

Therefore, surgical methods to reduce the likelihood of such pulmonary embolisms by actually blocking the blood clot from reaching the lungs have been developed. To this end, minimally invasive surgical techniques have been developed involving the placement of a mechanical barrier in the inferior vena cava. These barriers are in the form of filters and are typically inserted through either the femoral vein in the patient's leg or the right jugular vein in the patient's neck or arm under local anesthesia. The filters are then advanced intravascularly to the inferior vena cava where they are expanded to block migration of the blood clots from the lower portion of the body to the heart and lungs.

These prior filters take various forms. One type of filter is composed of coiled wires such as disclosed in U.S. Pat. Nos. 5,893,869 and 6,059,825. Another type of filter consists of legs with free ends having anchors for embedding in the vessel wall to hold the filter. These filters are disclosed, for example, in U.S. Pat. Nos. 4,688,553, 4,781,173, 4,832,055, and 5,059,205, 5,984,947 and 6,007,558. Another type of filter is disclosed in U.S. Pat. No. 6,214,025 consisting of wires twisted together to form a cylindrical anchoring portion conforming to the inner vessel wall surface to exert a radial force and a conical filtering portion.

Several factors have to be considered in designing vein filters. One factor is that the filter needs to be securely anchored within the vessel wall, while avoiding traumatic engagement and damage to the wall as well as damage to the neighboring abdominal aorta. Another factor is that the filter must be collapsible to a sufficiently small size to be easily maneuvered and atraumatically advanced intravascularly to the inferior vena cava or other target vessel. Thirdly, the filter should direct the blood clots to the center of the vessel to improve dissolution of the clot within the vessel by the blood flow.

The filters disclosed in the commonly assigned co-pending application Ser. No. 10/889,429 (hereinafter "the '429 application"), the entire contents of which are incorporated herein by reference, satisfy the foregoing parameters. The filters have sufficient anchoring force to retain the filter within the vessel while providing atraumatic contact with the vessel wall, have a minimized insertion (collapsed) profile to facilitate delivery through the vascular system to the surgical site, and direct migration of the captured blood clots to the center of the vessel. The filters also provide simplified insertion through the femoral or the right jugular vein or arm into the inferior vena cava.

The filters of the '429 application can advantageously be readily removed minimally invasively, e.g. intravascularly, from the patient, thus advantageously providing for a temporary filter. Thus, these filters advantageously strike the balance of having structure to provide sufficient anchoring while enabling atraumatic removal from the vessel after a period of time. Certain filters of the '429 application also advantageously have a retrieval end configured to facilitate grasping by a snare as well as to facilitate withdrawal by providing a smooth transition into a retrieval sheath.

The filters of the '429 are very effective in achieving their desired functions, whether used as a permanent or temporary filter. The present application provides a modification to the filters to even further facilitate removal if used as a temporary filter.

SUMMARY

The present invention provides modifications to the filters of the '429 application. The invention provides a vessel filter comprising a first distal region terminating at a first end of the filter and a second proximal region terminating at a second end of the filter, the filter movable between a collapsed position for delivery to the vessel and an expanded position for placement within the vessel. The first region has a filter portion having a converging region to direct particles toward the center of the filter and the second region is flared in the expanded position to have a transverse dimension increasing toward a second end portion opposite the filter portion, the second region including a vessel engaging portion at the second end portion. The first region has a retrieval hook and a spacer, wherein in the collapsed position the spacer extends axially in an elongated position distal of the retrieval hook and in the expanded position forms a looped region extending radially from the first region.

In a preferred embodiment, the first region includes a plurality of spaced apart elongated struts and a plurality of connecting struts extending at an angle from the elongated struts. Preferably, the spacer is formed from a cutout in the first region of the filter and encircles a distal region of the filter in the expanded position. In a preferred embodiment, the looped portion is an open loop.

In a preferred embodiment, the spacer is formed integrally with the filter and is formed of shape memory material.

Preferably, the converging region of the filter terminates in a tubular portion and each of the elongated struts in the first region extends outwardly from the tubular portion, the spacer in the expanded position extending radially from the tubular portion.

The present invention also provides a vessel filter comprising a body made from a single tube, the tube having a longitudinal axis and cut to create a plurality of elongated struts, and including a tubular region proximal of the struts and having a cut therein to form a radial spacer. The radial spacer extends substantially parallel to the longitudinal axis of the tube and distally beyond the tubular region in the collapsed position and extends radially outwardly from the tubular portion in a loop in the expanded position to space a retrieval region of the filter from a vessel wall. In a preferred embodiment, the loop is an open loop.

In a preferred embodiment, the spacer in the expanded position has a transverse dimension less than a transverse dimension of the filter in an expanded position. In a preferred embodiment, the spacer extends upwardly from the proximal end of a cut and continues downwardly to wrap around the tubular region. The spacer preferably has a looped shape memory position.

In one embodiment the vessel engaging hooks of the filter include a heel extending past the hook. The vessel engaging hooks can also have a plurality of teeth. In one embodiment the filter includes interconnecting struts in a filtering region of the body to form closed geometric shapes.

In a preferred embodiment, the retrieval region includes a hook having a cutout exposing an internal annular surface and vessel engaging hooks are positioned at the second region.

BRIEF DESCRIPTION OF THE DRAWINGS

Preferred embodiment(s) of the present disclosure are described herein with reference to the drawings wherein:

FIG. 1 is a perspective view of a first embodiment of the vein filter of the present invention in the collapsed (retracted) configuration, and shown removed from a delivery tube/sheath;

FIG. 2 is an enlarged broken side view of a portion of the vein filter of FIG. 1;

FIG. 3 is a developed view of the retention hooks of the vein filter of FIG. 1;

FIG. 4A is a perspective view of the vein filter of FIG. 1 in an expanded (radially extending) configuration;

FIG. 4B is a side view of the vein filter of FIG. 4A;

FIG. 5 is a front view of the vein filter of FIG. 4A;

FIG. 6 is a side view of the vein filter of FIG. 1 with the struts in the expanded configuration and the spacers in the collapsed configuration;

FIG. 7 is a close up perspective view of the detail of FIG. 6;

FIG. 8 is a perspective view of a cranial end of a filter of the '429 application showing the retrieval hook of the filter;

FIG. 9 is a view similar to FIG. 8 except showing the cranial end of the filter of FIG. 1, the spacers shown in the collapsed position;

FIG. 9A is a perspective view of an alternate embodiment of the retrieval portion of the filter having an extended hook;

FIG. 10 is a view similar to FIG. 9, except showing a broken view of the spacers extending radially from the tubular portion;

FIG. 11 is a perspective view of an alternate embodiment of the vein filter of the present invention having a single spacer loop, the filter and spacer shown in the expanded configuration;

FIG. 12 is a front view of the filter of FIG. 11;

FIGS. 13, 14, and 15 illustrate delivery and placement of the vessel filter of FIG. 1 in the inferior vena cava wherein FIG. 13 illustrates initial insertion of the delivery sheath through the femoral vein, FIG. 14 illustrates the delivery sheath being advanced toward the inferior vena cava just below (upstream) the juncture of the renal arteries; and FIG. 15 illustrates the filter in the expanded placement configuration in the inferior vena cava;

FIG. 15A illustrates an initial step in removal of the filter from the inferior vena cava by a retrieval snare and catheter;

FIG. 16 is a side view of an alternate embodiment of the filter of the present invention having spacers at different angles to the longitudinal axis of the filter, the spacers shown in the expanded position;

FIG. 17 is a perspective view of an alternate embodiment of the filter of the present invention having a single spacer extending in a single plane, the spacers shown in the expanded position;

FIG. 17A is a close up view of the area of detail of FIG. 17;

FIG. 18 is a perspective view of another alternate embodiment of the filter of the present invention having a single spacer extending in multiple planes;

FIG. 19 is a perspective view of the cranial end of another alternate embodiment of the filter of the present invention having two spacers, the spacers shown in the expanded position;

FIG. 19A is a view similar to FIG. 19 except showing the spacers in the collapsed position;

FIG. 20 is a perspective view of the cranial end of yet another alternate embodiment of the filter of the present invention having two spacers, the spacers shown in the expanded position;

FIG. 20A is a view similar to FIG. 20 except showing the spacers in the collapsed position;

FIG. 21 is a perspective view of the cranial end of another alternate embodiment of the filter of the present invention showing the two spacers in the expanded position;

FIGS. 22A-22C illustrate another alternate embodiment of the cranial end of the filter of the present invention wherein FIG. 22A is a perspective view of the cranial end in the collapsed configuration, FIG. 22B is a side view in the collapsed configuration and FIG. 22C is a perspective view in the expanded configuration;

FIG. 23 is a perspective view of an alternate embodiment of the vein filter of the present invention in the collapsed (retracted) configuration, and shown removed from a delivery tube/sheath;

FIG. 24 is a perspective view of the cranial or distal end of the filter of FIG. 23 shown within a delivery sheath;

FIG. 24A is a view similar to FIG. 24 showing partial deployment of the filter from the delivery sheath;

FIG. 25 is a perspective view of the vein filter of FIG. 23 in the expanded configuration; and FIG. 25A is an enlarged view of a region of the filter.

DETAILED DESCRIPTION OF PREFERRED EMBODIMENTS

Turning now to the drawings, wherein like reference numerals identify similar or like components throughout the several views, the vein filters of the present invention are described for placement within the inferior vena cava to capture blood clots or other particles which could otherwise pass to the lungs.

The filter is movable from a low profile collapsed configuration to facilitate insertion through the delivery sheath to a larger expanded placement configuration to enable atraumatic engagement with the vessel walls to secure (mount) the filter within the inferior vena cava. The filter is preferably substantially bell-shaped and preferably has a flared or mounting region (portion/section) and a filtering region (portion/section). The filtering region has inwardly directed struts, terminating in a converging region, thereby directing particles toward the central axis of the filter. By directing the particles to the center, they will be exposed to greater blood flow (since there is greater flow at the center than near the wall of the vessel) which improves dissolution of the particles. The filter increases in transverse dimension to form a flared region. The flare provides less contact area than a straight region, resulting in less tissue ingrowth to facilitate removal of the filter if desired. The flare also reduces the chance of vessel distortion if inserted into a curved vena cava. The filter also has one or more spacers to space the cranial end of the filter from the vessel wall to facilitate removal.

Turning now to details of the filter of the present invention and with initial reference to FIGS. 1 and 2, the filter is designated generally by reference numeral 10 and is shown in a collapsed configuration for delivery. Filter 10 is preferably formed from a single tube 11. In a preferred embodiment, the filter tube 11 is composed of shape memory material, such as Nitinol, a nickel titanium alloy, or elgiloy, however, other materials such as stainless steel are also contemplated. A plurality of cutouts are formed in the filter 10, preferably by laser cutting although other techniques are contemplated. In the illustrated embodiment, six elongated cutouts are formed, creating six strips or struts 14 of substantially uniform width separated by the cutouts.

The collapsed configuration of filter 10 reduces the overall profile to facilitate delivery to the site. The diameter or transverse dimension of filter 10 in the collapsed configuration is preferably about 2 mm and more preferably about 1.7 mm. Other dimensions are also contemplated. The filter is thus preferably dimensioned for insertion through a 6 French delivery system and through a 6 French catheter. The diameter or transverse dimensions of the filter in the expanded placement configurations (e.g. FIGS. 4A and 4B) is greater than the diameter or transverse dimension in the collapsed (delivery) configuration of FIG. 1.

FIGS. 4-5 illustrate the expanded placement configuration of the filter 10. FIGS. 6 and 7 illustrate the expanded configuration of the struts with the spacers in the collapsed position (not exposed from the sheath) to help illustrate the invention, a configuration that would occur briefly. Filter 10 is generally bell-shaped in configuration. Filter 10 has a flared region 17 and a converging region 21 at the filtering section 19. The transverse dimension of the filter at the flared (or mounting/anchoring) region 17 is greater than the transverse dimension at filtering section 19. Diameters (or transverse dimensions) preferably range from about 18 mm to about 32 mm, depending on the internal diameter of the vessel wall as will be explained in more detail below. Other dimensions are also contemplated. The elongated struts 14 are spaced apart as shown and extend at an angle away from the longitudinal axis L of filter 10 in region 17 to provide a flare. Preferably, this angle or taper is about 8°, although other dimensions are contemplated. When expanded, the six struts 14, as shown, are preferably spaced approximately 60 degrees apart. It is also contemplated that a fewer or greater number of struts and spacing other than 60 degrees be provided.

Filtering section 19 extends from the flared region 17, and extends toward the central longitudinal axis L of the filter 10 and converges into tubular portion 18 at the cranial end of the filter.

The struts 14 of filter 10 terminate in hooks 72a, 72b which extend substantially perpendicular from the strut, achieved by torquing the struts at the region 85 so the hooks bend out of the plane. A first set of hooks 72a is larger than a second set of hooks 72b. Preferably when formed in a laser cut tube, hooks 72a are formed so that they occupy a region equivalent to the transverse dimension of two adjacent struts. Smaller hooks 72b are spaced axially with respect to each other and axially inwardly with respect to larger hooks 72a as in the filter hooks of the '429 application to minimize the collapsed profile (transverse dimension) of the filter when collapsed for insertion. The penetrating tips 76a, 76b of hooks 72a, 72b, respectively, penetrate the tissue to retain the filter, preferably temporarily, and point distally, toward the cranial (or distal) end of the filter.

Each of the hooks 72a, 72b has a series of teeth 79a, 79b, respectively to engage the vessel wall to provide additional retention to prevent movement of the filter in the caudal direction. In a preferred embodiment, the larger hooks 72a have four teeth and the smaller hooks 72b have three teeth, although a different number of teeth could be provided. A heel 77a, 77b, is provided which extends past (proximally or caudal of) the respective hook 72a, 72b to function as a stop to prevent the filter strut portions from going through the vessel wall. The angle of the heel 77b in the smaller hooks 72b is less than the angle in the larger hooks 72a to provide room for nesting of the hooks as shown in FIG. 3. For clarity, not all of the hooks are fully labeled. Note this hook configuration with the teeth and/or heel can be utilized with the filters of the '429 application.

The six filter struts or strut portions 14 curve outwardly from tubular portion 18, extend radially therefrom and divide into two connecting filter struts or strut portions 14a, 14b (preferably of equal width, although differing dimensions are contemplated) that angle way from each other (in different directions) to extend to the connecting strut portion of an adjacent strut 14. Thus, connecting strut portion 14a of one strut 14 interconnects with the connecting strut portion 14b of an adjacent strut at joining region 14d. This forms closed geometric shapes 25, preferably substantially diamond shaped in configuration. For clarity, not all of the identical parts are labeled in the drawing.

In the illustrated embodiment, preferably six struts are provided forming twelve interconnecting struts, however a different number of struts and closed geometric shapes can be provided. Note that although all six struts 14 are shown interconnected, it is also contemplated that fewer than all the struts can be interconnected. Also, the strut width can vary as described with respect to the filters disclosed in the '429 application.

After convergence of strut portions 14a, 14b at joining region 14d, it transitions into elongated mounting strut portions 14c which form flared mounting or anchoring region 17. The length of the strut portions 14c in the anchoring region 19 can vary, with increased/decreased length increasing the flexibility/rigidity of the struts. The thickness of the strut portions can also vary to affect flexibility/rigidity.

As in the other embodiments described in the '429 applications, terms such as interconnected, joined, etc., are used for ease of description, it being understood that preferably these portions are integral as they are preferably formed from a single tube. Also, mounting struts and filter struts used to describe the various embodiments disclosed herein can be considered as mounting strut "portions" or "sections" and filter strut "portions" or "sections" of the same struts if the filter is formed integrally, e.g. from a cut tube.

The tubular portion 18 is preferably in the form of a retrieval hook 92 as described with respect to the embodiment of FIG. 20 in the '429 application. Other retrieval structure can also be utilized. Hook 92 is described in more detail below.

Two spiral cuts 45a, 45b are formed in the tube during manufacture, preferably by laser cutting, to enable two strips to be formed creating first and second spacers 40a, 40b for the filter. In the collapsed position, spacers 40a, 40b are in a substantially aligned position with respect to tubular portion 18, i.e. substantially flush with the tubular portion 18. Spacers 40a, 40b are maintained in this collapsed position during delivery to the surgical site. (See e.g. FIG. 1). The spacers 40a, 40b have a shape memorized position forming loops as shown in FIG. 4A. Thus, once exposed from the delivery sheath, the spacers 40a, 40b move from their collapsed position to their shape memory looped position of FIGS. 4A, 4B and 5. The surface 42a, 42b of the loop of each spacer 40a, 40b engages opposite sides (lying approximately 180° apart) of the vessel wall to maintain centering of the cranial end of the filter and to space tubular portion 18 and retrieval hook 92 away from the vessel wall. This spacing prevents tissue ingrowth around the hook, thereby making it easier to grasp and remove filter 10.

The loops of spacers 40a, 40b are open, somewhat oval shaped loops, terminate in ends 44a, 44b and lie in substantially alternate spiral planes. The first strip cut into tubular portion 18 unravels from a proximal end 48a of cutout 45a to a distal end 46a of cutout 45a to form spiral spacer 40a (see e.g. FIGS. 4B and 7). The second strip cut into tubular portion 18 unravels from a proximal end 48b of cutout 45b to a distal end 46b of cutout 45b to form spiral spacer 40b. In the FIG. 4 embodiment, the spacer loops 40a, 40b lie in planes that are substantially perpendicular to the longitudinal axis L of the tubular portion 18 and filter 10. However, alternatively the spacer loops could lie in planes at angles other than 90 degrees and could lie in planes not parallel to each other. Examples of different angles of spacer loops with respect to the longitudinal axis of the tubular portion of the filter are shown by way of example in FIG. 16. Two angled spacer loops (e.g. about 75 degrees) are designated by reference numeral 70' and smaller acute angled spacer loops, (e.g. about 45 degrees) are designated in phantom by reference numeral loop 70". The other components of the filter are identical to filter 10 and are designated with corresponding prime (') reference numerals.

A comparison of FIGS. 8-10 illustrates that in the preferred embodiment, the length of tubular portion 18 remains substantially unchanged once the filter is implanted, even with the addition of the spacers. FIG. 8 illustrates a cranial end of a filter of the '429 application showing the retrieval hook H of the filter. The tubular portion P has a length L1 preferably ranging from about 0.100 inches to about 0.600 inches, and preferably about 0.300 inches. The tubular portion 18 of FIG. 9, which is the embodiment of FIG. 1, has a length L2, preferably ranging from about 0.500 inches to about 1.700 inches, and preferably about 0.881 inches which is greater than length L1 due to the space needed to create the spiral spacers 40a, 40b. However, once the spacers 40a, 40b move from their aligned position to their expanded position, the end of the tubular portion 18 contracts to close the gap created by the spiral cutouts to move to a length L3 which is preferably closed to length L1.

FIGS. 11 and 12 illustrate an alternate embodiment of the filter, designated by reference numeral 110. Filter 110 is identical to filter 10, except for the tubular portion and spacer, and therefore has been labeled with numerals in the "100" series corresponding to the double digit numbering of filter 10. Thus, filter 110 has struts 114, interconnecting struts 114a, 114b, hooks 172a, 172b, etc. and therefore for brevity these parts will not again be described.

Tubular portion 150 of filter 110 has a hook 192 identical to hook 92 of FIG. 1. However, tubular portion 150 has a single spiral cutout 152, preferably formed by laser cutting, which forms a spiral spacer 154. The spiral spacer 154 has a shape memory position of that shown in FIGS. 11 and 12, extending radially from the tubular portion 150. When exposed from the sheath it unravels to move from a collapsed position substantially flush with the tubular portion 150 to its shape memory position forming an open loop starting at end 155 and wrapping over 360 degrees, terminating at edge 157. In this manner loop portions 156 and 158 are 180 degrees apart and the circular loop surfaces contact the inner wall of the vessel. It is also contemplated that the spacer can wrap a smaller or greater distance (degrees) than that shown and be oval or shapes other than circular. The loop can lie in a single plane or in multiple planes.

FIG. 17 discloses an alternate embodiment of the filter which is identical to the filter shown in FIG. 11 except for the spiral spacer 264. The filter 210 is labeled with reference numerals in the "200 series" corresponding to the "100 series" labeled parts of the FIG. 11 embodiment and therefore has struts 214, hooks 272a, 272b, etc. The tubular portion and spacer, being different, have non-correlating reference numerals. More specifically, tubular portion 260 has a spiral cutout 262 to form a spacer 264. The distal (cranial) terminal end 266 of the cutout 262 has an increased width to form a spacer end 269 of increased width "w", shown in FIG. 17A. This provides increased support for the spacer as it reduces stress at that part. Spiral spacer 264 loops around tubular portion 260 in a similar manner as spacer 154 of FIG. 11, preferably wrapping over 360 degrees, although other degrees are contemplated. Opposed looped ends 267 and 269 are about 180° apart and the outer surfaces contact opposing sides of the vessel wall. As with spacers 254, the outer surfaces along the loop contact the vessel wall due to the circular configuration of the spacer 264.

In the embodiment of FIG. 18, the spacer 364 of filter 310 wraps around the tubular portion 360 in different planes, as opposed to the single plane of the embodiment of FIGS. 11 and 17. More specifically, in the expanded position, spacer 364 emerges from the distal (cranial) end 366 of cutout 365 and wraps at an angle toward the caudal end of the filter. Thus, as seen, the first end 372 of loop portion 370 lies in a plane proximal of the plane containing end 371 of loop portion 370 and distal of the plane containing the end 374 of loop portion 376. In other words, loop portion 378 lies, as viewed axially, between loops 370, 376. The remaining portions of the filter are identical to filter 210 of FIG. 17 and are labeled with corresponding parts in the "300" series.

FIGS. 19 and 19A illustrate the cranial end of an alternate embodiment of the filter having two looped spacers extending radially from the tubular portion 324. In the collapsed position of FIG. 19A, spacers 320, 322 are wrapped around tubular portion 324 so they are substantially flush with the wall of the tubular portion 324. The spacers 320, 322 are formed by two spiral cutouts 326, 328 formed in the wall of tubular portion 324. In the expanded position, spacer 320 emerges from the proximal (caudal) end 329 of cutout 328, extending in a substantially circular or spiral path around the tubular portion 324, preferably for about 300 degrees (although other degrees are contemplated), with surfaces 321, 323 about 180° apart contacting opposing surfaces of the vessel wall. Spacer loop 320 terminates at end 323 to form an open loop. Spacer 322 emerges from the distal (cranial) end of the cutout 326, wrapping around tubular portion 324 in the direction opposite of spacer 320. Similar to spacer 320, spacer 322 extends for about 300 degrees (although other degrees are contemplated), with opposing surfaces 325, 327 contacting opposite portions of the vessel wall. Spacer loop 322 terminates at end 331 to form an open loop. Hook 330 is preferably identical to hook 92 of the filter embodiment of FIG. 1.

In the embodiment of FIG. 20, open spacer loops 420 and 422 each start at a proximal end of cutout 426, with spacer 420 starting proximal of spacer 422. Cutout 426 has first cutout 426*a* and second cutout 426*b*, formed in an alternating pattern. Spacers 420, 422 lie in multiple planes, preferably wrap around tubular portion 424 in opposite directions, extending for about 300 degrees (although other degrees are contemplated) and have respective opposing surfaces 421, 423 and 425, 427, respectively for contacting opposing sides of the vessel wall. Spacers 420, 422 terminate in ends 430, 432.

In the embodiment of FIG. 21, open spacer loops 520, 522 are formed emerging from the distal end of cutouts 526*a*, 526*b*, with spacer 520 emerging distal of spacer 522. Spacers 520, 522 lie in different planes. Similar to loops 420, 422 of the embodiment of FIG. 21, spacer 520 has opposing surfaces 521 and 523 and spacer 522 has opposing surfaces 525, 527. Loops 520, 522 lie in multiple planes.

In the embodiment of FIG. 22, open spacer loops 620, 622 extend from the distal end of cutout 626*a*, 626*b*. As shown, the cutouts are formed in an intertwined spiral fashion resulting in a spiral spacer when unraveled (expanded). The solid strip between cutout 626*a* is designated by reference numeral 630 and the solid strip between cutout 626*b* is designated by reference numeral 632.

FIGS. 23-25 illustrate an alternate embodiment of the filter. Filter 710 is identical to filter 10, except for the tubular portion at the cranial end and the spacer, and therefore has been labeled with numerals in the "700" series corresponding to the double digit numbering of filter 10. Thus, filter 710 has struts 714, interconnecting struts 714*a*, 714*b*, struts 714*c* in the mounting region terminating in hooks 772*a*, 772*b*, closed cells 725, etc. and therefore for brevity these parts will not again be described.

Tubular region 801 has cutout 803 extending from proximal cutout end 805 to opening 807 in the tubular region 801. Spacer 810 extends from the cutout end 805 upwardly from the tubular region 801, with a curved transition 811, and then (as viewed in FIGS. 25 and 25A) wraps under the tubular region 801 and encircles the tubular region as it forms a loop 812. Preferably the loop 812 is an open loop such that in the expanded position it wraps around in a loop less than 360 degrees, although wrapping to other degrees, including 360 degrees or more, is also contemplated. Preferably the loop 812 in the expanded configuration is substantially perpendicular to a longitudinal axis of the filter, i.e. an axis parallel to a longitudinal axis of the filter passes through the opening 814.

In the delivery position, as shown in FIGS. 24 and 24A, the spacer 810 is elongated, extending distally from the tubular region 801 and preferably along an axis substantially parallel to a longitudinal axis of the filter 700 and tubular region 801. When the filter is exposed from the delivery sheath D, the spacer 810 forms the looped shape as shown in FIG. 25. As with the other described filters described herein, filter 800 is preferably made of shape memory material and formed by laser cutting a shape memory tube. However, other materials are also contemplated.

In one method of manufacturing the filter 800, two filters with spacers 810 are formed from a section of shape memory tube. That is, the same section of tube can be used to from a spacer for one filter and spacer for a second filter. More specifically, a tube would be laser cut so that a first filter is formed in the direction of FIG. 23, so the spacer extends to the left as viewed in the Figure, and the second filter is formed in the opposite direction so the spacer would extend to the right as viewed in FIG. 23. In this manner, the spacers are formed adjacent one another from the same section of tube.

To enable movement between an expanded and collapsed configuration, the filter of the embodiments described herein, as noted above, is preferably made of shape memory metal material, such as Nitinol, a nickel titanium alloy, and preferably manufactured from a laser cut tube. To facilitate passage of the filter through the lumen of the delivery sheath 700 (shown in FIG. 13 in conjunction with the method of insertion) and into the vessel, cold saline is injected into the delivery sheath or catheter 700 and around the filter in its collapsed position within the delivery sheath 700. This shape memory material characteristically exhibits rigidity in the austenitic state and more flexibility in the martensitic state. The cold saline maintains the temperature dependent filter in a relatively softer condition as it is in the martensitic state within the sheath. This facilitates the exit of filter from the sheath 700 as frictional contact between the filter and the inner surface of the sheath would otherwise occur if the filter was maintained in a rigid, i.e. austenitic, condition.

Once ejected from the delivery sheath or catheter 700, the filter is no longer cooled and is exposed to the warmer body temperature, which causes the filter to return towards its austenitic memorized configuration.

In the placement (expanded) configuration, the filter moves towards its memorized position and the extent it returns to its fully memorized position will be dependent on the size of the vessel in which the filter is inserted. (The larger the vessel, the closer the filter comes to returning to it's fully memorized position). The extent of movement of the spacer(s) to its fully memorized position could also be limited by the size of the vessel.

The filter can be inserted through the jugular vein in the neck of the patient or through the femoral vein in the leg of the patient or the arm. The filters can also be placed in the superior vena cava.

FIGS. 13-15 illustrate delivery and placement of the filter 10, by way of example, in the inferior vena cava. Delivery catheter or sheath 700 is inserted through the femoral vein "f" and advanced through the iliac arteries into the inferior vena cava. Delivery catheter 700 is withdrawn once the tip of the sheath is adjacent the structure so that withdrawal of the sheath would place the filter in the desired location of FIG. 15. Tubing 704 and valve assembly 706 enable saline injection. Delivery catheter 700 is withdrawn to enable filter 10 to be warmed by body temperature to transition to the expanded placement configuration. The other filters described herein could be inserted in the same manner. Note it is implanted in the orientation such that filter section 19 is downstream of the flared section 17. This enables blood clots or other particles to be directed to the center of the filter section by the angled struts. Thus the direction of insertion, e.g. upstream or downstream direction, will determine how the filter is to be positioned in the delivery catheter.

The foregoing filters can be removed from access through the internal jugular or femoral vein. Various methods can be used to remove the filter such as those described in commonly assigned co-pending '429 application, the entire contents of which is incorporated herein by reference, including for example, slotted hooks, graspers, etc.

A recess or cutout is preferably provided at the tubular end portion to form a hook portion 90, as shown for example in FIGS. 7 and 9, having a curved hook 92 at the proximalmost end to receive a snare or other device for removal as described in the filter of the '429 application.

This hook 92 is configured to receive a retrieval snare or other retrieval device. A portion of the wall of the hook 90 is cut out to expose the annular interior surface 94. This annular interior surface 94 extends from radiused region 95 to proximalmost edge 96. The interior surface 94, for ease of explanation, can be considered to have an interior surface at the radiused region 95 and an interior surface 94b at the hook 92. The interior surface 94b accommodates a portion of a tubular snare sheath. That is, the outer wall of the snare sheath (tube) can partially fit within the cut out region. This enhances removal as the snare pulls the filter hook into collinear arrangement with the sheath tube as described and shown in FIGS. 13H-13N of the '429 application. The radiused region 95, spaced axially (distal) from the hook 92, includes a radiused or curved edge defined by radiused side walls 97a, 97c and top wall 97b. The angled side walls 97a, 97c form camming surfaces to direct the hook 90 and filter into the retrieval sheath.

When the filter is grasped by the retrieval device and pulled distally to disengage from the vessel walls, the spacers flex inwardly. This is shown for example in FIG. 15, wherein spacers 40a, 40b of filter 10 flex in the direction of the arrow as the filter is pulled into retrieval sheath 800.

It should be appreciated, that the hook can be formed in other ways to provide an interior annular surface to function in a similar manner as surface 94, i.e. to receive the snare tube. When the filter is pulled into the retrieval sheath it is collapsed for removal.

FIG. 9A illustrates an alternate embodiment of the hook portion 600 having an elongated hook 602 curving inwardly. This provides increased hooking area for the retrieval snare.

To facilitate removal of the filter from the vessel, cold saline can be injected onto the implanted filter to change the temperature of the filter to move it to a relatively softer condition to facilitate the filter being drawn into the retrieval sheath. That is, injection of cold saline will cause the filter to approach its martensitic state, bringing the filter to a more flexible condition. The flexible condition facilitates the collapse and withdrawal of the filter into the retrieval sheath by decreasing the frictional contact between the filter and the inner surface of the retrieval sheath.

A delivery system which can be used for the filter of the present invention which includes a filter cartridge, is shown and described in the '429 application.

While the above description contains many specifics, those specifics should not be construed as limitations on the scope of the disclosure, but merely as exemplifications of preferred embodiments thereof. For example, the foregoing filters can be inserted in other regions of the body. Also, the foregoing filters can be made of materials other than shape memory material. Those skilled in the art will envision many other possible variations that are within the scope and spirit of the disclosure as defined by the claims appended hereto.

What is claimed is:

1. A vessel filter comprising a first distal region terminating at a first end and a second proximal region terminating at a second end of the filter, the filter movable between a collapsed position for delivery to a vessel and an expanded position for placement within the vessel, the first distal region having a filter portion having a converging region to direct particles toward a center of the filter, the second proximal region being flared in the expanded position to have a transverse dimension increasing toward a second end portion opposite the filter portion, the second proximal region including a vessel engaging portion at the second end portion, the first distal region having a tubular portion and having a retrieval hook and a spacer, wherein in the collapsed position the spacer extends axially in an elongated position distal of the retrieval hook and in the expanded position forms a looped region extending radially from the first distal region and looping around the tubular portion, wherein the looped region is an open loop.

2. The vessel filter of claim 1, wherein the first distal region includes a plurality of spaced apart elongated struts and a plurality of connecting struts extending at an angle from the elongated struts.

3. The vessel filter of claim 1, wherein the spacer is formed from a cutout in the first distal region of the filter.

4. The vessel filter of claim 3, wherein the spacer encircles a distal region of the filter the expanded position.

5. The vessel filter of claim 1, wherein the spacer is formed integrally with the filter and is formed of shape memory material.

6. The vessel filter of claim 1, wherein the vessel engaging portion includes vessel engaging hooks having a plurality of teeth.

7. The vessel filter of claim 6, wherein the vessel engaging hooks include a heel extending past the hook.

8. The vessel filter of claim 1, wherein the filter is formed from a laser cut tube and composed of shape memory material.

9. The vessel filter of claim 1, wherein the converging region terminates in the tubular portion and the filter includes a plurality of elongated struts, each of the elongated struts in the first distal region extends outwardly from the tubular portion, the spacer in the expanded position extending radially from the tubular portion.

10. The vessel filter of claim 1, wherein the first region further includes a retrieval region, the retrieval hook has a cutout exposing an internal annular surface, the annular surface dimensioned to receive a portion of a retrieval sheath.

11. The vessel filter of claim 1, wherein the loop extends for greater than 360 degrees around the tubular portion.

12. A vessel filter comprising a body made from a single tube and movable between a collapsed position and an expanded position, the body having a longitudinal axis and cut to create a plurality of elongated struts, the body further including a tubular region proximal of the struts and having a cut therein to form a radial spacer, the radial spacer extending substantially parallel to the longitudinal axis of the body and distally beyond the tubular region in the collapsed position and extending radially outwardly in a loop from the tubular region in the expanded position to space a retrieval region of the filter from a vessel wall, the loop extending around the tubular region, wherein the loop is an open loop.

13. The vessel filter of claim 12, wherein the filter includes interconnecting struts in a filtering region of the body to form closed geometric shapes.

14. The vessel filter of claim 12, wherein the spacer in the expanded position has a transverse dimension less than a transverse dimension of a remaining portion of the filter in an expanded position.

15. The vessel filter of claim 14, wherein the spacer extends upwardly from a proximal end and continues downwardly to wrap around the tubular region.

16. A vessel filter comprising a body made from a single tube and movable between a collapsed position and an expanded position, the body having a longitudinal axis and cut to create a plurality of elongated struts, the body further including a tubular region proximal of the struts and having a cut therein to form a radial spacer, the radial spacer extending substantially parallel to the longitudinal axis of the body and distally beyond the tubular region in the collapsed position and extending radially outwardly in a loop from the tubular region in the expanded position to space a retrieval region of the filter from a vessel wall, the loop extending around the tubular region, wherein the loop extends for greater than 360 degrees around the tubular portion.

17. The vessel filter of claim 16, wherein the spacer in the expanded position has a transverse dimension less than a transverse dimension of a remaining portion of the filter in an expanded position.

18. The vessel filter of claim 16, wherein the filter includes interconnecting struts in a filtering region of the body to form closed geometric shapes.

* * * * *